US010602671B2

(12) United States Patent
Limpert et al.

(10) Patent No.: US 10,602,671 B2
(45) Date of Patent: Mar. 31, 2020

(54) GAS-DELIVERY LIGHT FIXTURE AND METHOD FOR MAKING AND USING

(71) Applicant: Grow Lites, LLC, Eden Prairie, MN (US)

(72) Inventors: Matthew P. Limpert, Bloomington, MN (US); Barbara A. DeBaun, Woodbury, MN (US); Walter J. Paciorek, Phoenix, AZ (US); John T. Golle, Eden Prairie, MN (US); Charles A. Lemaire, Apple Valley, MN (US)

(73) Assignee: Grow Lites, LLC, Eden Prairie, MN (US)

( * ) Notice: Subject to any disclaimer, the term of this patent is extended or adjusted under 35 U.S.C. 154(b) by 0 days.

(21) Appl. No.: 15/987,857

(22) Filed: May 23, 2018

(65) Prior Publication Data
US 2019/0223386 A1    Jul. 25, 2019

Related U.S. Application Data

(60) Provisional application No. 62/621,041, filed on Jan. 23, 2018.

(51) Int. Cl.
*A01G 7/04* (2006.01)
*F21V 33/00* (2006.01)
(Continued)

(52) U.S. Cl.
CPC .............. *A01G 7/045* (2013.01); *A01C 23/00* (2013.01); *A01G 7/02* (2013.01); *A01G 9/025* (2013.01);
(Continued)

(58) Field of Classification Search
CPC . A61L 2209/12; A01G 7/045; F21V 33/0044; F21V 31/0088; F21V 31/0096;
(Continued)

(56) References Cited

U.S. PATENT DOCUMENTS 6,095,661 A     8/2000  Lebens et al.
7,607,815 B2   10/2009  Pang
(Continued)

FOREIGN PATENT DOCUMENTS

JP        2012120477 A   6/2012
WO    WO 2017024079       2/2017
WO    WO 2018089955       5/2018

OTHER PUBLICATIONS

Heliospectra, Intelligent Lighting Solutions for Optimal Plant Growth and Energy Efficiency, Jan. 2016, pp. 1-72 (see attached pdf).*
(Continued)

*Primary Examiner* — Navin Natnithithadha
*Assistant Examiner* — Sunita Reddy
(74) *Attorney, Agent, or Firm* — Charles A. Lemaire; Jonathan M. Rixen; Lemaire Patent Law Firm, P.L.L.C.

(57) ABSTRACT

A plant-light system that includes a plurality of ducted plant-lighting plenum sheets, wherein each ducted plant-lighting plenum sheet includes a plurality of flexible perforated LED sheets, each LED sheet including a plurality of LEDs arranged on a grid, the plurality of LEDs including LEDs emitting light that appears red, light that appears blue, light that appears white, and light that is at least mostly infrared light, wherein each plant lighting sheet has a length and a width, and wherein the plurality of lighting sheets is arranged along a length of a room; a plurality of plant-holding pockets arranged along the length of the room generally parallel to the plurality of ducted plant-lighting plenum sheets; and a plant-lighting plenum sheets motion and withdrawal system arranged to move the plurality of ducted plant-lighting plenum sheets to a plurality of different locations relative to the plurality of plant-holding pockets for different time periods.

22 Claims, 12 Drawing Sheets

(51) Int. Cl.
*A01C 23/00* (2006.01)
*A61M 21/02* (2006.01)
*F21V 19/00* (2006.01)
*A01G 7/02* (2006.01)
*A01G 9/24* (2006.01)
*A01G 9/02* (2018.01)
*A61M 21/00* (2006.01)
*F21Y 113/13* (2016.01)
*F21Y 115/10* (2016.01)
*F21Y 105/10* (2016.01)
*F21V 23/00* (2015.01)

(52) U.S. Cl.
CPC ............. *A01G 9/246* (2013.01); *A61M 21/00* (2013.01); *A61M 21/02* (2013.01); *F21V 19/003* (2013.01); *F21V 33/0056* (2013.01); *F21V 33/0096* (2013.01); *A61M 2021/0016* (2013.01); *A61M 2021/0044* (2013.01); *A61M 2021/0066* (2013.01); *A61M 2021/0077* (2013.01); *A61M 2202/0208* (2013.01); *A61M 2205/587* (2013.01); *F21V 23/001* (2013.01); *F21Y 2105/10* (2016.08); *F21Y 2113/13* (2016.08); *F21Y 2115/10* (2016.08)

(58) Field of Classification Search
CPC .......... F21V 29/60; F21V 29/61; F21V 29/67; F21V 29/673; F21V 29/677; F21Y 2105/10; F21Y 2115/10; F21Y 2107/70; F21W 2131/30; F24F 13/078; F32V 29/60; A61F 2/852; A61F 2/07; A61F 2002/075; A61F 2240/001; A61F 2002/061; A61F 2220/0075
USPC ........... 600/26–28; 607/88; 47/48.5, 581 LS, 47/577; 362/6, 563, 122
See application file for complete search history.

(56) References Cited

U.S. PATENT DOCUMENTS

| | | | |
|---|---|---|---|
| 7,617,857 B2 | 11/2009 | Froese | |
| 8,454,991 B2 | 6/2013 | Woo et al. | |
| 8,471,274 B2 | 6/2013 | Golle et al. | |
| 9,116,276 B2 | 8/2015 | Montfort et al. | |
| 9,282,699 B2 | 3/2016 | Anderson et al. | |
| 9,474,217 B2 | 10/2016 | Anderson et al. | |
| 9,510,524 B2 | 12/2016 | Anderson et al. | |
| 9,700,641 B2* | 7/2017 | Hawkins ............ H05B 33/0854 | |
| 9,814,186 B2 | 11/2017 | Anderson et al. | |
| 9,903,574 B2 | 2/2018 | Golle et al. | |
| 9,974,243 B2 | 5/2018 | Martin | |
| 2001/0028227 A1* | 10/2001 | Lys ..................... A61N 5/0616 315/317 |
| 2003/0189829 A1* | 10/2003 | Shimizu .................... F21L 4/00 362/240 |
| 2005/0212439 A1* | 9/2005 | Zampini .................. F21K 9/00 315/86 |
| 2006/0275721 A1* | 12/2006 | Starr ....................... F21S 10/04 431/125 |
| 2010/0115830 A1* | 5/2010 | Dube ..................... A01G 7/045 47/17 |
| 2011/0049266 A1* | 3/2011 | Jorgensen ................. A61L 9/03 239/338 |
| 2011/0062482 A1 | 3/2011 | Solomensky et al. |
| 2011/0079660 A1* | 4/2011 | Jorgensen ................. A61L 9/14 239/144 |
| 2011/0088314 A1* | 4/2011 | Jacobs ..................... A01G 9/22 47/32.3 |
| 2011/0101883 A1* | 5/2011 | Grajcar ................... A01K 29/00 315/291 |
| 2011/0175533 A1* | 7/2011 | Holman .................... E04B 9/32 315/130 |
| 2011/0241559 A1* | 10/2011 | Grajcar ................... A01K 1/00 315/250 |
| 2013/0082298 A1* | 4/2013 | Golle ..................... H01L 29/18 257/99 |
| 2014/0090295 A1 | 4/2014 | Fambro |
| 2014/0098538 A1 | 4/2014 | De Vaal |
| 2014/0226329 A1* | 8/2014 | Oraw ................. H01L 25/0753 362/235 |
| 2014/0332990 A1* | 11/2014 | Brosmith ............ B01F 3/04085 261/142 |
| 2015/0021632 A1 | 1/2015 | Taghizadeh et al. |
| 2015/0128488 A1* | 5/2015 | Casper .................... A01G 7/045 47/58.1 LS |
| 2015/0305108 A1* | 10/2015 | Probasco ............... A01G 22/00 47/58.1 LS |
| 2015/0305252 A1* | 10/2015 | Klase ...................... F21V 5/007 362/231 |
| 2016/0154170 A1* | 6/2016 | Thompson ........ G02F 1/133603 362/609 |
| 2016/0178179 A1* | 6/2016 | Hanson ..................... A01G 2/00 362/249.02 |
| 2017/0105265 A1* | 4/2017 | Sadwick ............... A61N 5/0618 |
| 2017/0238401 A1* | 8/2017 | Sadwick .................. A61N 5/01 315/294 |
| 2017/0241632 A1* | 8/2017 | Nguyen .................. F21V 29/59 |
| 2017/0307242 A1* | 10/2017 | Handsaker ............... F24F 11/89 |
| 2018/0008172 A1 | 1/2018 | Mycek et al. |
| 2018/0135840 A1 | 5/2018 | Golle et al. |
| 2018/0352755 A1* | 12/2018 | Szoradi .................. A01G 7/045 |

OTHER PUBLICATIONS

"PCT Search Report/Written Opinion for related PCT/US2019/014641 application, dated Jul. 9, 2019, 13 pages.".

* cited by examiner

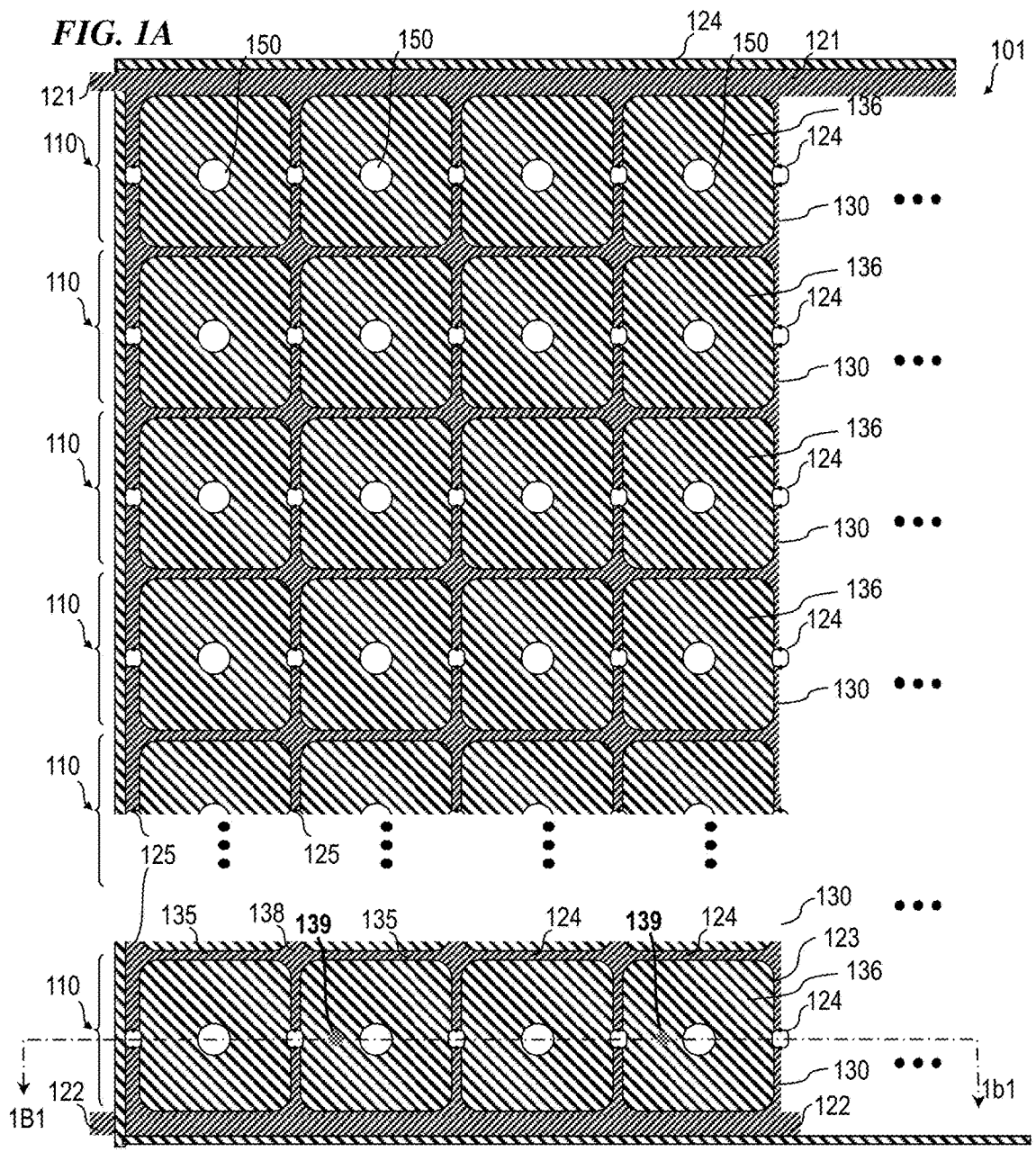
FIG. 1A
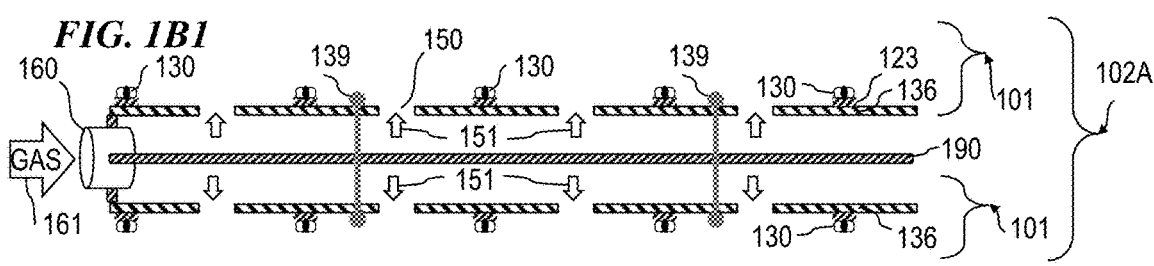
FIG. 1B1

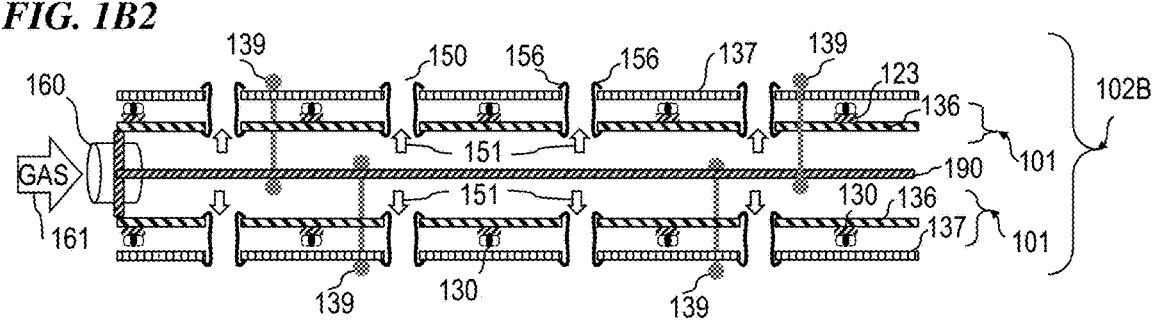
*FIG. 1B2*
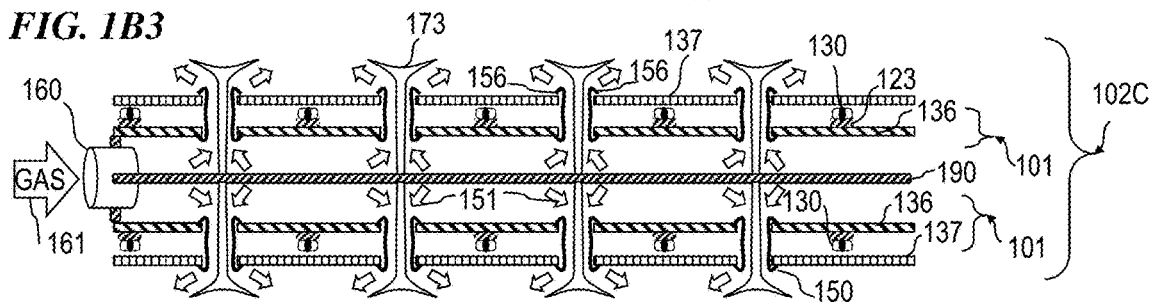
*FIG. 1B3*
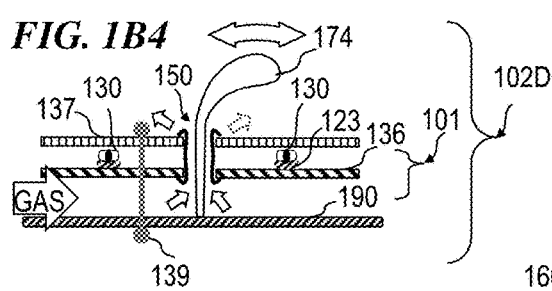
*FIG. 1B4*
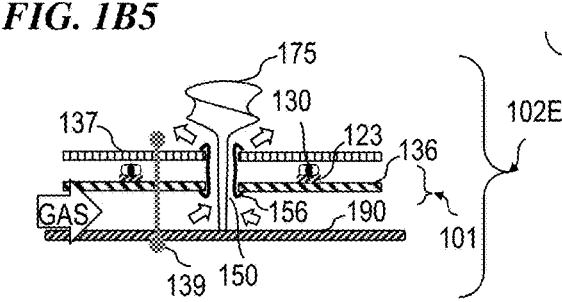
*FIG. 1B5*
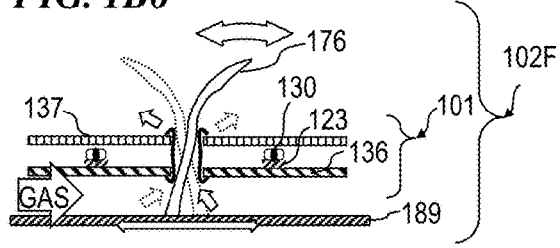
*FIG. 1B6*
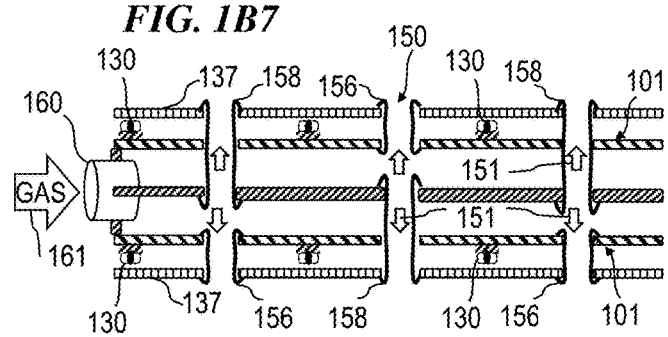
*FIG. 1B7*
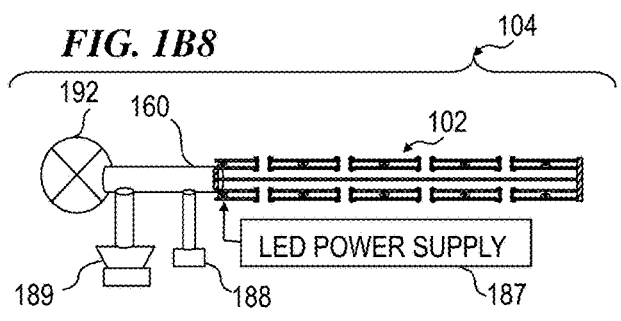
*FIG. 1B8*

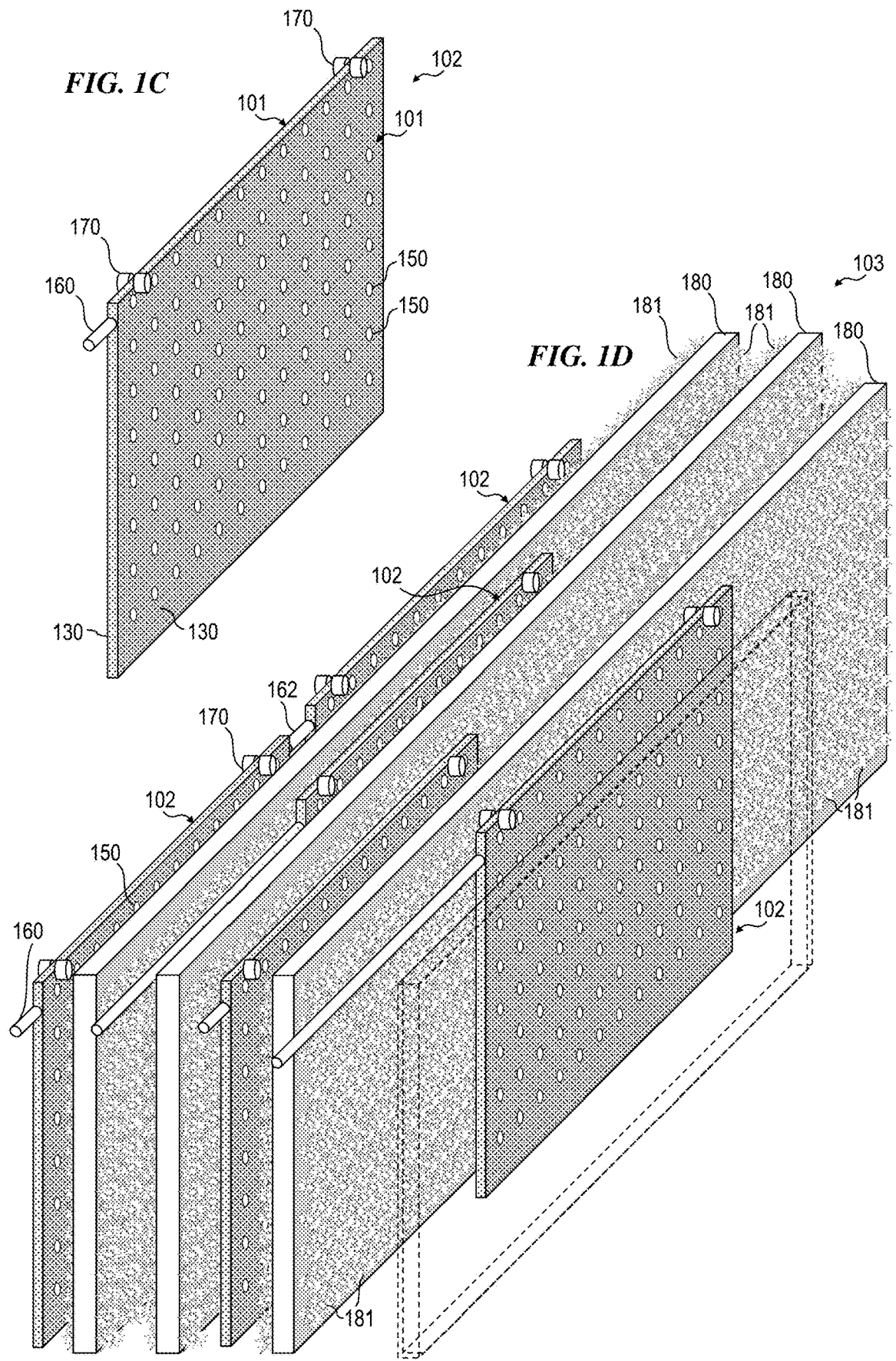

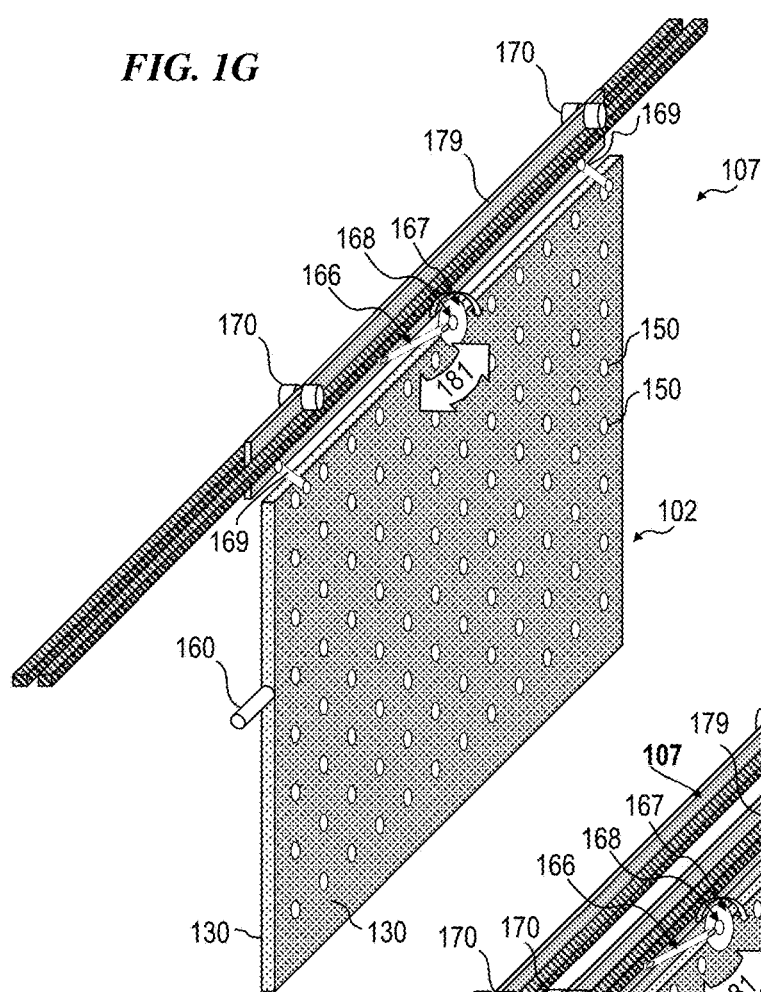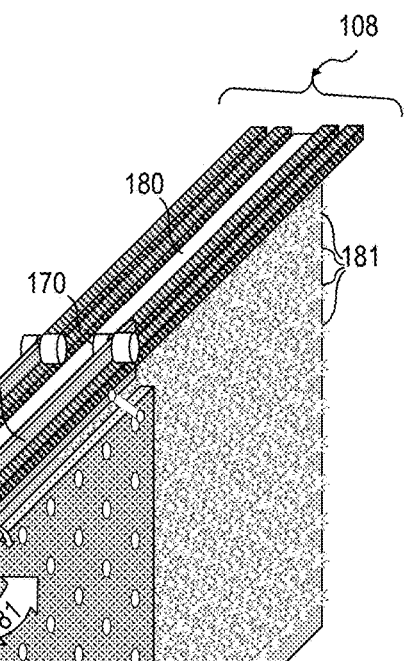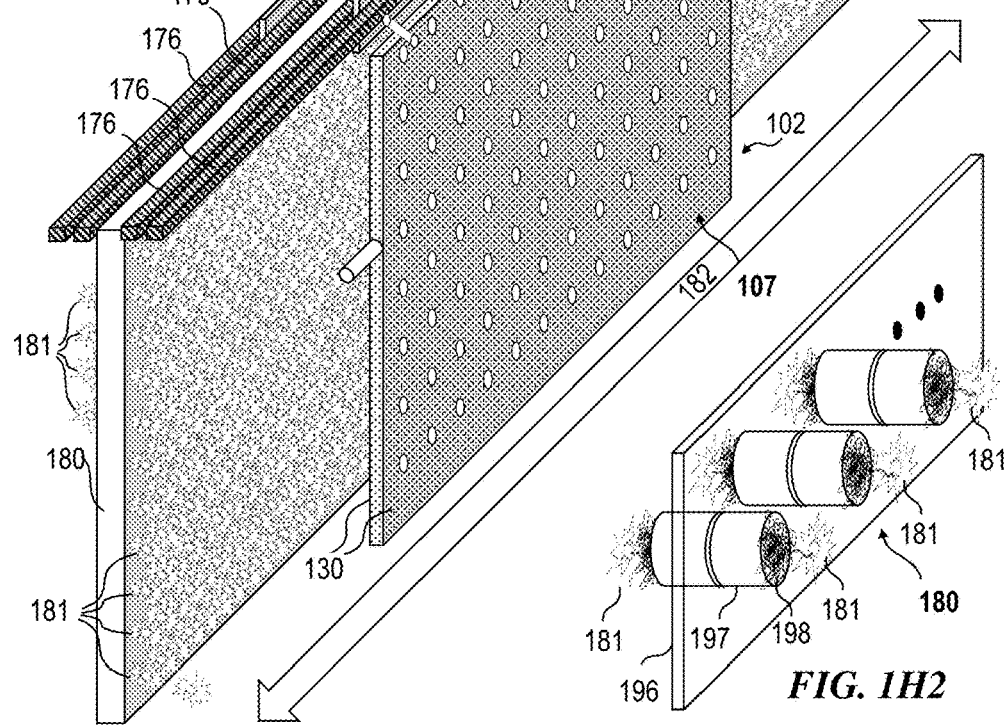

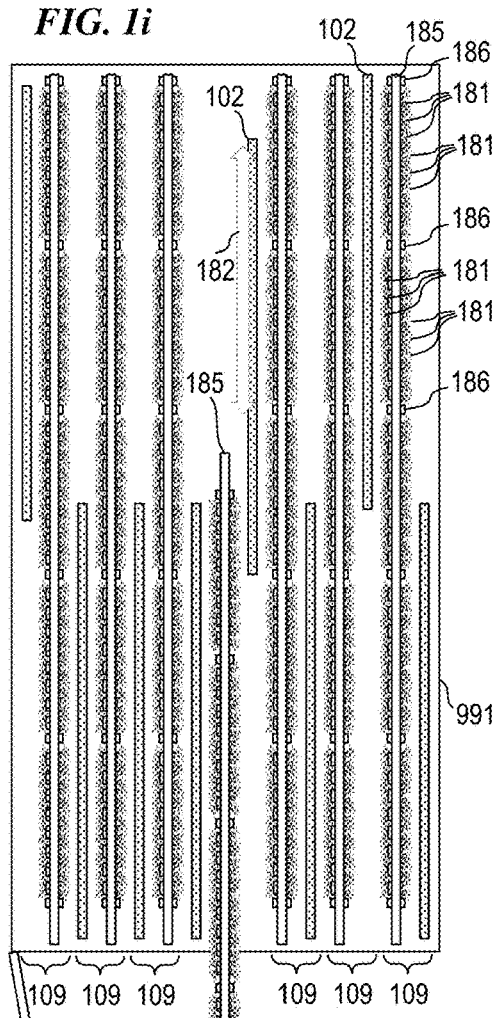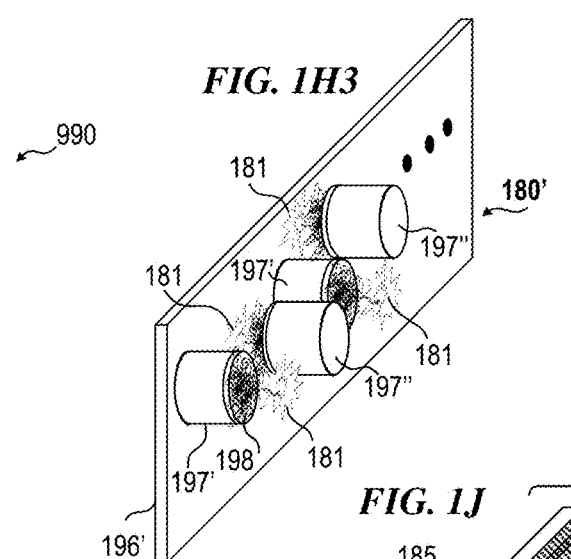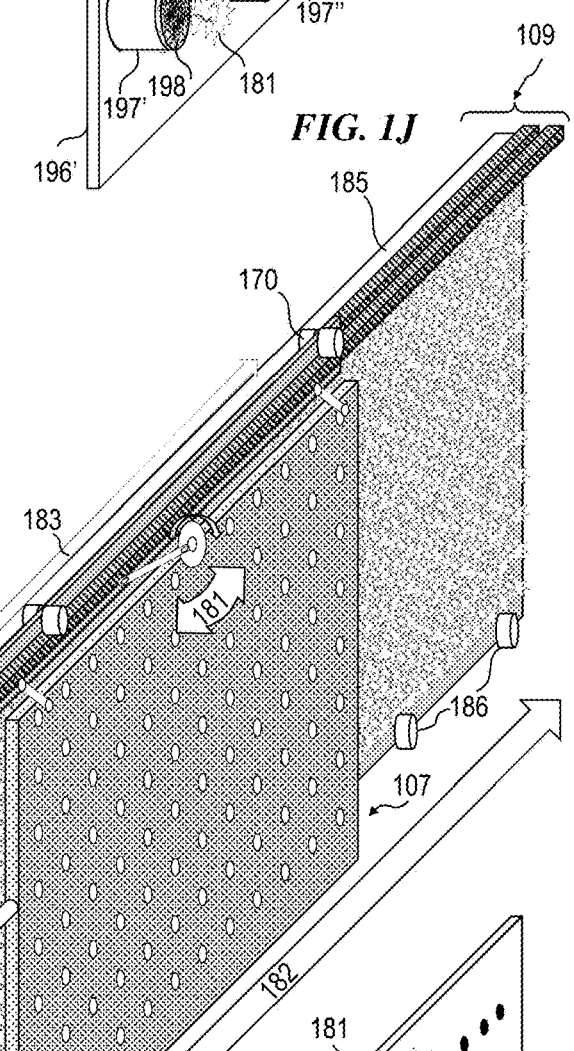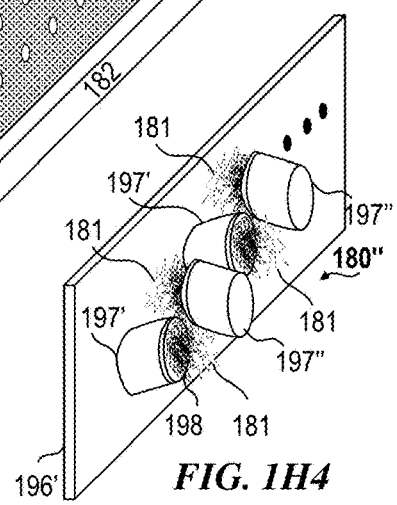

*FIG. 4A1* 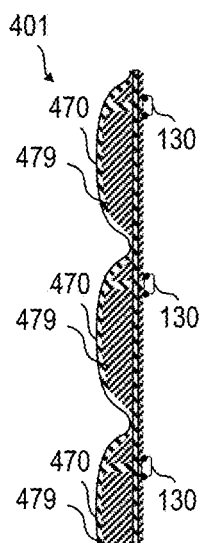 *FIG. 4B1* 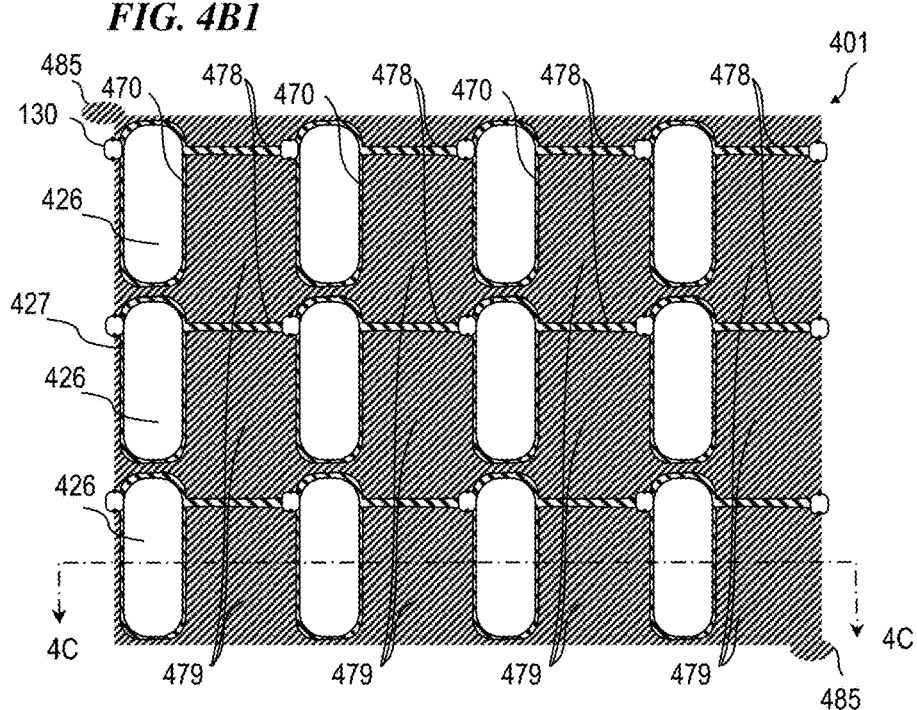
*FIG. 4C1* 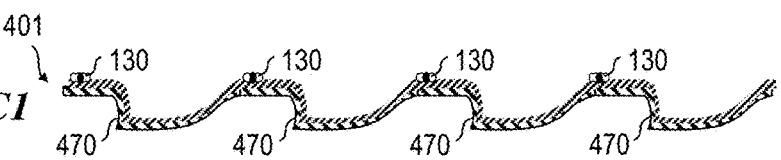
*FIG. 4A2* *FIG. 4B2* 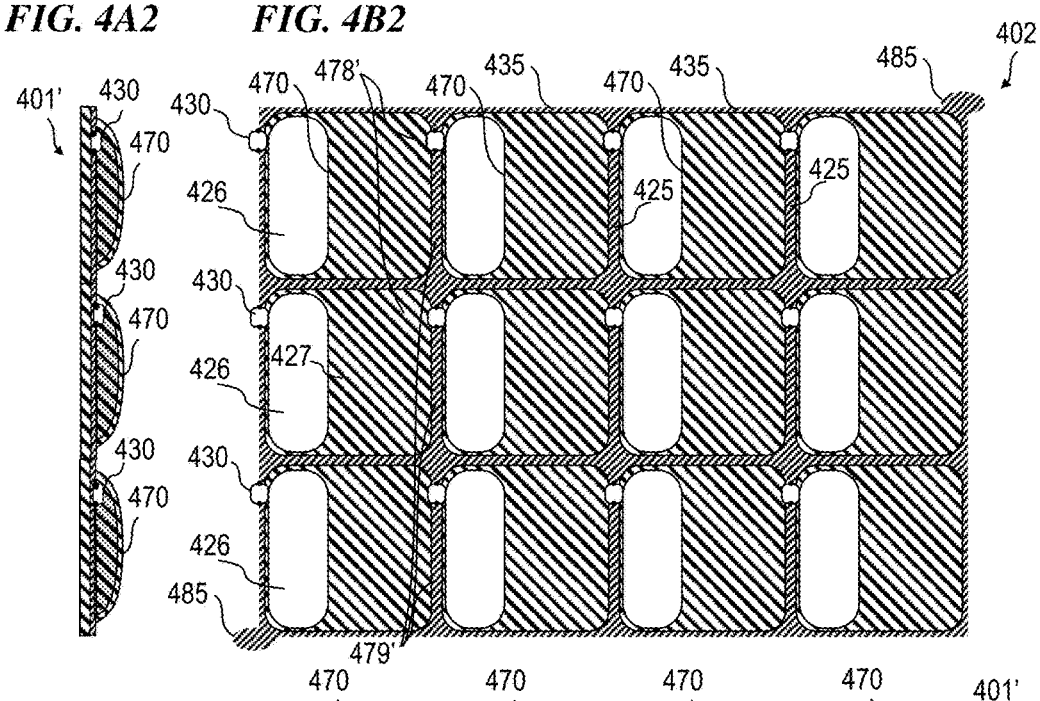
*FIG. 4C2* 

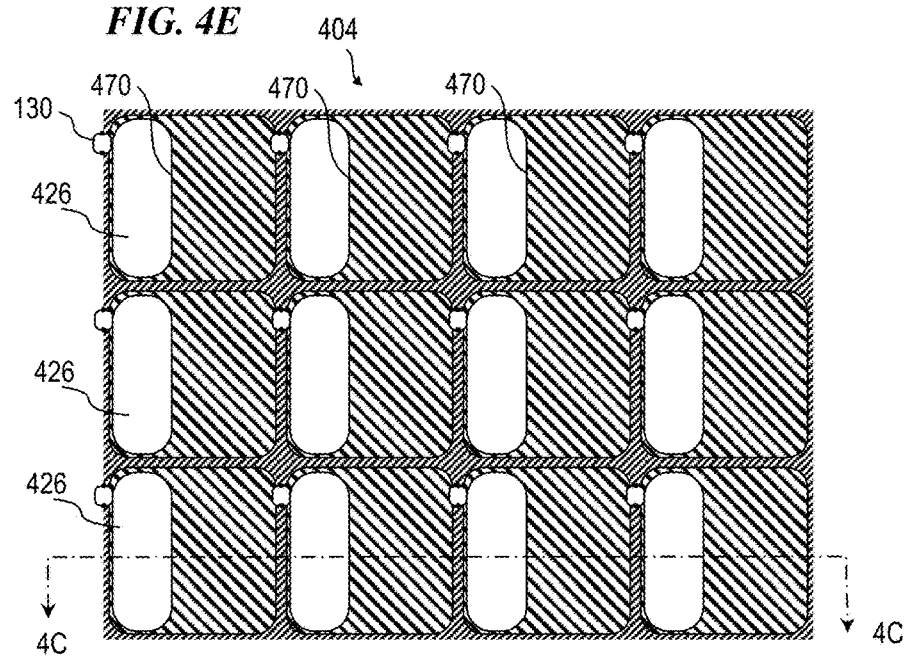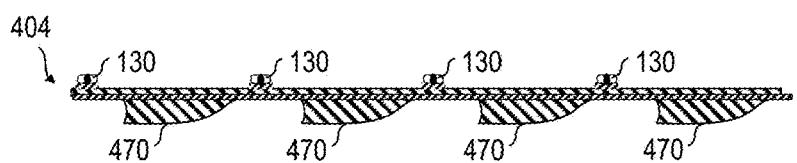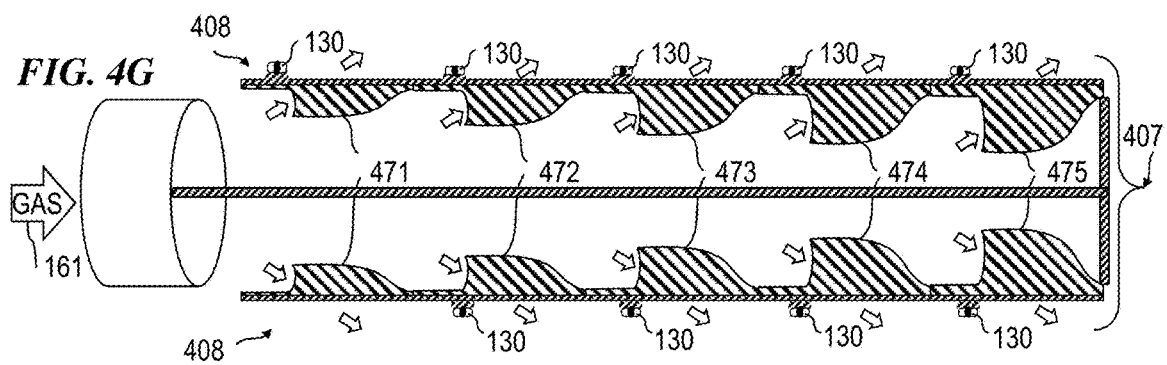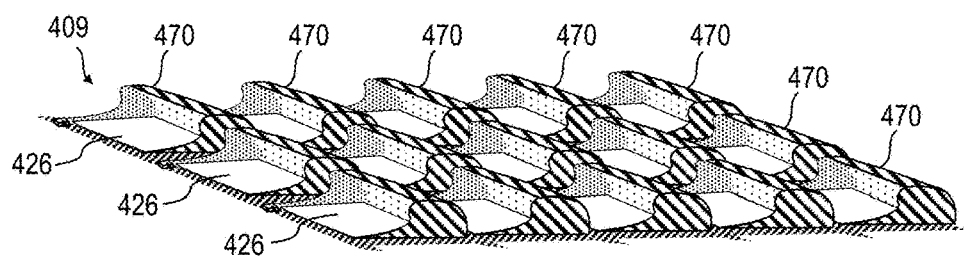

GAS-DELIVERY LIGHT FIXTURE AND METHOD FOR MAKING AND USING

CROSS-REFERENCE TO RELATED APPLICATIONS

This application claims priority benefit, under 35 U.S.C. § 119(e), of U.S. Provisional Patent Application No. 62/621,041, filed Jan. 23, 2018 by Matthew P. Limpert, et al., titled "Gas-delivery light fixture and method for making and using," which is incorporated herein by reference in its entirety.

This invention is related to
U.S. Provisional Patent Application No. 62/421,970 filed Nov. 14, 2016 by Michael C. Naylor et al., titled "Plant growth lighting system and method,"
U.S. Provisional Patent Application No. 62/486,444 filed Apr. 17, 2017 by John T. Golle et al., titled "Plant growth lighting system and method,"
U.S. Provisional Patent Application No. 62/574,172 filed Oct. 18, 2017 by John T. Golle et al., titled "Lighting fixture and method for making and using,"
U.S. Provisional Patent Application No. 62/574,193 filed Oct. 18, 2017 by John T. Golle et al., titled "Lighting fixture and method for making and using,"
U.S. Provisional Patent Application No. 62/574,194 filed Oct. 18, 2017 by John T. Golle et al., titled "Lighting fixture and method for making and using,"
U.S. Provisional Patent Application No. 62/576,646 filed Oct. 24, 2017 by John T. Golle et al., titled "Lighting fixture and method for making and using,"
U.S. Provisional Patent Application No. 61/894,495 filed Oct. 23, 2013 by Aaron J. Golle et al., titled "High powered LED light module with a balanced matrix circuit,"
Publication WO/2015/061332 of P.C.T. Patent Application No. PCT/US2014/061594 filed Oct. 21, 2014 by Aaron J. Golle et al., titled "High powered LED light module with a balanced matrix circuit,"
U.S. Pat. No. 9,903,574 to Aaron J. Golle et al. issued on Feb. 27, 2018 with the title "High powered LED light module with a balanced matrix circuit" (from U.S. patent application Ser. No. 15/031,564 filed Apr. 22, 2016 by Golle et al.), titled "High powered LED light module with a balanced matrix circuit,"
U.S. Pat. No. 8,471,274 issued Jun. 25, 2013 to Aaron J. Golle, et al. with the title "LED light disposed on a flexible substrate and connected with a printed 3D conductor,"
PCT Publication WO/2018/089955, published May 17, 2018, of P.C.T. Patent Application No. PCT/US2017/061416 filed Nov. 13, 2017 by John T. Golle et al., titled "Lighting fixture and method for making and using,"
U.S. Patent Application Publication US 2018/0135840, published May 17, 2018, of U.S. application Ser. No. 15/811,660 filed Nov. 13, 2017 by John T. Golle et al., titled "Acoustic-control light fixture and method for making and using" (which issued as U.S. Pat. No. 10,215,387 on Feb. 26, 2019),
which are all incorporated herein by reference in their entirety.

FIELD OF THE INVENTION

The present invention relates to devices and methods for lighting, and in particular to a lighting system and methods for making and using the lighting system for such applications as architectural lighting, light-assisted aroma therapy, and gas-supplemented agricultural lighting for enhanced growth of plants to improve time to harvest, plant size, and plant quality, and to obtain better taste, smell and/or potency of products from the plants, and in some embodiments, the present invention provides a skinny air plenum covered on one or both opposing faces with one or more perforated flexible plant-illumination sheets, which optionally include air scoops, for use in controlled-environment agriculture.

BACKGROUND OF THE INVENTION

One problem with LED (light-emitting-diode) illumination of large areas with a large amount of light is to manage the heat from the LED devices, and in particular, to prevent the large temperature rise associated with locating a large number of LED devices in a small area, to efficiently power the devices from a low-cost power supply, and to provide a low-cost substrate on which to mount the LED devices.

Architectural building lighting often needs different spectra of light and different amounts of light for different times of the day. The need for different spectra of light and different amounts of light for different times of the day also applies for light supplied to crop plants and therapy lighting for seasonal affective disorder (SAD therapy).

The conventional approach for home growers of plants is to select lighting depending on the types and quantity of plants they grow. As a general rule, inexpensive lights tend to be the most expensive to operate and least effective in promoting plant growth. Home growers typically choose fluorescent to grow herbs and to germinate flowering varieties. High-pressure sodium (HPS) lights or metal halide (MH) lights are often chosen for commercial-scale indoor growing of plants, but these high-wattage systems create excessive heat and consume excessive energy. All of these sources generate much heat and much of their light is in wavelengths that are not efficiently used by plants.

Some light-emitting-diode (LED) grow lights maximize blue and red light to provide a balance for plants, but high initial purchase cost has prohibited mass adoption for home growers. In addition, even conventional LED grow lights are driven with high current, often consuming 100 to 300 watts of electrical power, which leads to excess heat, forcing growers to keep the LEDs 18 to 30 or more inches away from the plants (which uses up valuable volumetric indoor space) and to use fans and air conditioning (involving further cost and volumetric space) in order to remove harmful excess heat.

U.S. Pat. No. 9,903,574 to Aaron J. Golle et al. issued on Feb. 27, 2018 with the title "High powered LED light module with a balanced matrix circuit," and is incorporated herein by reference. U.S. Pat. No. 9,903,574 describes inventive embodiments that include a device for distributing power to devices over an area, with a power density of at least one Watt per ft$^2$ (or 900 cm$^2$ in metric units). The device includes a flexible substrate; a circuit that includes a thin film conductor having a thickness of 400 nanometers or less, wherein the circuit is adhered to the substrate; a plurality of devices positioned on the sheet and attached to the circuit wherein each device of the plurality is driven at substantially the same voltage; and the power delivered to the devices is at least 90% of the input power of the energized circuit.

U.S. Pat. No. 8,471,274 to Aaron J. Golle, et al. issued on Jun. 25, 2013 with the title "LED light disposed on a flexible substrate and connected with a printed 3D conductor," and is incorporated herein by reference. U.S. Pat. No. 8,471,274 describes a flexible planar substrate including a first surface that is planar, at least one bare light-emitting-diode ("LED") die coupled to the substrate and conductive ink electrically coupling the at least one bare LED die, wherein the conductive ink is disposed on the substrate and extends onto a surface of the LED that is out-of-plane from the first surface.

U.S. Pat. No. 7,607,815 to Pang issued on Oct. 27, 2009 with the title "Low profile and high efficiency lighting device for backlighting applications" and is incorporated herein by reference. U.S. Pat. No. 7,607,815 describes a light source having a flexible substrate and a plurality of dies having LEDs is disclosed. The light source can be conveniently utilized to provide an extended light source by bonding the light source to a suitable light pipe. The substrate is divided into first and second regions. The dies are bonded to the substrate in a first region. A portion of the surface of the substrate in the second region is reflective. The substrate is bent such that the second region forms a reflector that reflects light that would otherwise be emitted in a non-useful direction to a more useful direction. The substrate can be constructed from a three-layer flexible circuit carrier in which the dies are mounted on a bottom metal layer to provide an improved thermal path for heat generated in the dies.

U.S. Pat. No. 7,617,857 to Froese issued Nov. 17, 2009 with the title "Illuminated window blind assembly" and is incorporated herein by reference. U.S. Pat. No. 7,617,857 describes an illuminated blind assembly having either horizontally oriented slats or vertically oriented slats. The slats have structure that allows them to be illuminated. The slats can be A.C. or D.C. powered. The window blind assembly may have a housing containing rechargeable batteries. These batteries can be charged by photovoltaic solar cells that are positioned on the top surfaces of the slats. The window blind assembly can have a tilt/raise/lower pulley system structure and electrical servos in a housing extending across the top of the window blind assembly. An infrared remote sensor can be located in the front of the housing for controlling the electric servos and the switch for lighting up the slats.

U.S. Pat. No. 9,116,276 to Montfort et al. issued on Aug. 25, 2015 with the title "Room divider with illuminated light guide blind blade" and is incorporated herein by reference. U.S. Pat. No. 9,116,276 describes an apparatus that includes a first holder configured to hold a light source and having an interface for receiving power to feed to said light source, and a light guide plate configured to be coupled to said first holder and guide light emitted by the light source out from at least one surface of the light guide plate.

U.S. Pat. No. 8,454,991 to Woo et al. issued on Jun. 4, 2013 with the title "Method and device for photodynamic therapy," and is incorporated herein by reference. U.S. Pat. No. 8,454,991 describes a photodynamic therapy method and uses thereof for treating an individual in need thereof, including administering a photosensitizer to an individual and activating the photosensitizer with a chemiluminescent light source, and/or a light-emitting diode light source, wherein the light source is in dermal contact with the individual. The light source is a chemiluminescent light source or a light-emitting diode light source and the device is adapted to deliver the photosensitizer to the individual and to irradiate a part of an individual to activate the photosensitizer.

U.S. Pat. No. 9,282,699 to Anderson, et al. issued on Mar. 15, 2016 with the title "Irrigation system," and is incorporated herein by reference. U.S. Pat. No. 9,282,699 describes an irrigation system that includes a carriage may move along a predetermined path in a reciprocal manner. The carriage supports one or more exit ports that are fed plant growth material by a pressurized delivery arrangement. One or more plant stands are configured and arranged to straddle the carriage as it moves along the predetermined path. The one or more plant stands form a chamber into which plant roots may extend, and into which the one or more exit ports are able to discharge their plant growth material. The one or more plant stands may include side panels and a cap to reduce infiltration of light and contaminants, and to enhance the plant root-plant growth material interface and absorption rates. The carriage and/or the plant stand(s) may include friction reducing elements that facilitate transverse movement. The carriage and/or the plant stand(s) may be supported by a modular framework.

U.S. Pat. No. 9,474,217 to Anderson, et al. issued on Oct. 25, 2016 with the title "Controlled environment and method," and is incorporated herein by reference. U.S. Pat. No. 9,474,217 describes an irrigation system that may include a carriage that may move along a predetermined path in a reciprocal manner. The carriage may support one or more exit ports that may be fed nutrient supply by a pressurized delivery arrangement. One or more plant stands may be configured and arranged to straddle the carriage as it moves along the predetermined path. The one or more plant stands may form a chamber into which plant roots may extend, and into which the one or more exit ports may discharge their nutrient supply. The one or more plant stands may include side panels and a cap to reduce infiltration of light and contaminants and to enhance the plant root/nutrient supply interface and absorption rates. The carriage and/or the plant stand(s) may include friction reducing elements that facilitate transverse movement. The carriage and/or the plant stand(s) may be supported by framework.

U.S. Pat. No. 9,814,186 to Anderson et al. issued on Nov. 14, 2017 with the title "Growing system," and is incorporated herein by reference. U.S. Pat. No. 9,814,186 describes a growing system and/or plant support structure that may include one or more feet supporting at least one or more uprights, on which a plurality of plants and/or grow boards for growing plants may be positioned. A nutrient delivery system may be positioned between opposing uprights to provide nutrient supply to a root zone of plants, which nutrient delivery system may be positioned adjacent each opposing upright in an interior chamber of the plant support structure. A light system may be positioned between two adjacent plant support structures such that it simultaneously provides light to the exterior surface of the two plant support structures.

U.S. Pat. No. 6,095,661 to Lebens, Bourn and Lemaire issued on Aug. 1, 2000 with the title "Method and apparatus for an L.E.D. flashlight," and is incorporated herein by reference. U.S. Pat. No. 6,095,661 describes an improved method and apparatus for hand-held portable illumination. An illumination source includes a housing, a plurality of LEDs, and an electrical circuit that selectively applies power from the DC voltage source to the LED units, wherein the illumination source is suitable for handheld portable operation by a user. In one embodiment, the first electrical circuit further includes a control circuit for controlling a light spectrum and maintaining a predetermined light output level of the LED units as a charge on a battery varies. In another embodiment, the control circuit maintains an average predetermined light output level of the LED units as the charge on the battery cell varies by changing a pulse width or frequency as the charge on the battery cell varies to maintain a given average light output. Another aspect provides an illumination source that includes a light-emitting diode (LED) housing including one or more LEDs, and a control circuit that selectively applies power from a source of electric power to the LEDs, the control circuit substantially maintaining a light output characteristic of the LEDs as a voltage of the voltage source varies over a range that would otherwise vary the light output characteristic. Still another aspect provides an illumination source including a light-emitting diode (LED) housing including one or more LEDs; and a control circuit that selectively applies power from a source of electric power to the LEDs, thus maintaining or controlling a light output color spectrum of the LEDs.

What is needed is a more efficient and effective lighting solutions having air-flow and/or other capabilities that are useful for architectural lighting as well as for growing plants, particularly in large mass-production warehouse indoor growing facilities.

SUMMARY OF THE INVENTION

The present invention provides one or more skinny lighted gas-delivery ducts or plenums having outer walls made of perforated flexible LED illumination sheets, each supporting an array of LEDs that are interconnected in parallel and in series. In some embodiments, the perforated LED sheet is thermo-formed such that each respective perforation includes an air scoop to redirect a predetermined or desired amount of the supplied gas through that respective perforation with a given directionality. In some embodiments, the LEDs are mounted as bare LED dice that are electrically connected to electrical conductors on the substrate.

Some embodiments include a plant-light system that includes a plurality of ducted plant-lighting plenum sheets, wherein each ducted plant-lighting plenum sheet includes a plurality of perforated LED tiles (e.g., in some embodiments, flexible polymer substrates having copper circuitry used to electrically connect to the LEDs), each LED tile including a plurality of LEDs arranged on a grid, the plurality of LEDs including LEDs emitting light that appears red, light that appears blue, light that appears white, and light that is at least mostly infrared light, wherein each plant lighting sheet has a length and a width, and wherein the plurality of lighting sheets is arranged along a length of a room; a plurality of plant-holding pockets arranged along the length of the room generally parallel to the plurality of ducted plant-lighting plenum sheets; and a plant-lighting plenum sheets motion and withdrawal system arranged to move the plurality of ducted plant-lighting plenum sheets to a plurality of different locations relative to the plurality of plant-holding pockets for different time periods.

Some embodiments include a lighting apparatus that includes a flexible circuit substrate that has a front face and an opposite back face, and a first end and an opposite second end; a first plurality of LEDs on the flexible substrate, wherein each die of the first plurality of LEDs emits blue light; a second plurality of LEDs that emits red light; a third plurality of LEDs that emits infrared, wherein the first, second and third plurality of LEDs each emit a full-width-half-maximum bandwidth of no more than 50 nm in each of their respective colors. Some embodiments provide variable spacing to the apparatus and variable scheduled lighting periods and accommodate various types of botanical plants.

In some embodiments, the present invention is used to enhance plant growth, and the supplied gas delivered through the perforations in the gas-delivery light fixture includes air and/or carbon dioxide and/or water mist and/or other plant nutrients in gas or vapor form, and the lighted gas-delivery plenums form movable light-delivery and gas-delivery functions in narrow aisles between vertical racks of crop plants, such as lettuce, spinach or herbs indoors in a large warehouse-type structure. In some embodiments, the gas is thermally regulated to provide, e.g., cooled air to compensate for the small amount of heat generated by the LEDs on the perforated LED sheets, or warmed air for cold climates.

In some embodiments, the present invention is used in a lighted gas-delivery therapy device for treatment of humans or other animals, such as for seasonal affective disorder (SAD) therapy. In some such embodiments, the gas includes air (in some embodiments, temperature-regulated air), and/or one or more aromatherapy agents in gas or vapor form, and/or one or more photosensitizer agents, and optionally including an enhanced oxygen content, and the lighted gas-delivery plenum provides table-top SAD light- and gas-delivery functions. In some embodiments, the gas is thermally regulated to provide, e.g., a therapeutic cooling or warming airflow that is controlled by a patient based on the patient's self-perceived needs.

In some embodiments, the parallel-series interconnections connect rows of LEDs in parallel, wherein each LED in a given row has substantially the same voltage drop and substantially the same current through the respective LED, but wherein different rows of LEDs can provide different voltage drops (such as red and/or infrared LEDs that typically have a relatively low voltage drop (for example, about 2.0 to 2.4 volts depending on device type), in contrast to green, cyan, blue, violet or ultraviolet LEDs that have relatively higher voltage drops (for example, 2.8 to 3.5 volts depending on device type) and a plurality of such rows are connected in series from a common voltage supply or current supply conductor to a common ground conductor. In some embodiments, there are no required conductor crossings of the parallel-series interconnections, so a single single-layer conductor pattern is deposited on the substrate, reducing the cost of the substrate.

In some embodiments, the parallel-series interconnections are arranged in a rectangular grid (e.g., in some embodiments, a grid of squares), and in the center of each grid rectangle or square, the substrate is removed, leaving a rectangle or square opening, optionally having rounded corners to help prevent tearing that can otherwise occur if the corners were sharp.

In some embodiments, the movable skinny air-delivery ducts having outer walls made of perforated flexible LED illumination sheets of the present invention are used in narrow-aisled controlled-environment agriculture (CEA) applications.

In some embodiments, the present invention further includes air-movement actuators (such as air-driving pistons, audio speakers, subwoofers and/or the like operatively coupled to the air-delivery duct(s) and/or plenums), and/or actuators that move the lighted movable skinny air-delivery ducts having outer walls made of perforated flexible LED illumination sheets or outward facing sheets made of perforated flexible LED illumination sheets located within one or more outer covering sheets or protective layers that are at least partially transparent to the wavelengths of interest. In some embodiments, the wavelengths of interest for plant-growing applications include red, white and blue wavelengths and optionally cyan, green, yellow, violet, ultraviolet (UV) and/or infrared (IR) wavelengths. In some embodiments, the air-movement actuators and/or audio speakers are used to output sound vibrations of about 600 Hz to promote plant pollination. In other embodiments, sound vibrations in a range between 300 and 900 Hz, are used. In some embodiments, these sound vibrations are pulsed (modulated by a pulse envelope). In some embodiments, the air supply is pulsed using an air-motion device such as a piston to periodically move the leaves and stems of the crop plants.

Certain marks referenced herein may be common-law or registered trademarks of applicant or the assignee, or of third parties affiliated or unaffiliated with the applicant or the assignee. Use of these marks is for providing a descriptive and enabling disclosure by way of example and shall not be construed to limit the scope of the claimed subject matter to material, services or products associated with such marks.

BRIEF DESCRIPTION OF THE FIGURES

FIG. 1A is a front view of perforated plant light sheet 101, according to some embodiments of the present invention.

FIG. 1B1 is a top cross-sectional view of a portion of assembled gas-delivery plenum plant light apparatus 102A, according to some embodiments of the present invention.

FIG. 1B2 is a top cross-sectional view of a portion of plant light apparatus 102B having a clear polymer cover 137 and a plurality of push-pin type air-pore devices 156, according to some embodiments of the present invention.

FIG. 1B3 is a top cross-sectional view of a portion of plant light apparatus 102C having a clear polymer cover 137 and a plurality of air-pore devices 156 having T-shaped air dispersers 173, according to some embodiments of the present invention.

FIG. 1B4 is a top cross-sectional view of a portion of plant light apparatus 102D having a clear polymer cover 137 and a plurality of air-pore devices 156 having flapper air dispersers 174, according to some embodiments of the present invention.

FIG. 1B5 is a top cross-sectional view of a portion of plant light apparatus 102E having a clear polymer cover 137 and a plurality of air-pore devices 156 having spiral-shaped air dispersers 175, according to some embodiments of the present invention.

FIG. 1B6 is a top cross-sectional view of a portion of plant light apparatus 102F having a clear polymer cover 137 and a plurality of air-pore devices 156 having flapper air dispersers 176 on a mover device 189, according to some embodiments of the present invention.

FIG. 1B7 is a top cross-sectional view of a portion of plant light apparatus 102G having a clear polymer cover 137, a plurality of short air-pore devices 156 connecting the clear polymer cover 137 to the perforated plant light sheet 101, and a plurality of long air-pore devices 158 connecting the clear polymer cover 137 to the perforated center sheet 190, according to some embodiments of the present invention.

FIG. 1B8 is a schematic top cross-sectional view of a skinny gas-delivery plant light system 104 having a gas-movement unit 192 (such as a gas pump, fan or other actuator) and an assembled gas-delivery plant light apparatus 102, according to some embodiments of the present invention.

FIG. 1C is an orthographic view of assembled plant light apparatus 102, according to some embodiments of the present invention.

FIG. 1D is an orthographic view of a plant-growth system 103 utilizing a plurality of assembled plant light apparatuses 102, according to some embodiments of the present invention.

FIG. 1G is an orthographic view of a swinging assembled plant light apparatus 107, according to some embodiments of the present invention.

FIG. 1H1 is an orthographic view of a plant-growth system 108 utilizing a plurality of swinging assembled plant light apparatus 107, according to some embodiments of the present invention.

FIG. 1H2 is an orthographic view of a small sub-portion of plant-holder system 180, according to some embodiments of the present invention.

FIG. 1H3 is an orthographic view of a small sub-portion of plant-holder system 180', according to some embodiments of the present invention.

FIG. 1H4 is an orthographic view of a small sub-portion of plant-holder system 180", according to some embodiments of the present invention.

FIG. 1i is a plan view of an enclosed plant-growth container apparatus 990, according to some embodiments of the present invention.

FIG. 1J is an orthographic view of a plant-growth system 109 utilizing a plurality of swinging plant light apparatuses 107 and a plurality of movable plant walls 185, according to some embodiments of the present invention.

FIG. 3 is a top view of plant light system 301, with a plurality of parallel tracks for variable light-to-plant spacings, according to some embodiments of the present invention.

FIG. 4A1 is an end view of a portion of a perforated light-sheet 401 with air scoops 470 and large metal areas 479 adjacent the LEDs 130, according to some embodiments of the present invention.

FIG. 4B1 is a plan view of a portion of perforated light-sheet 401, according to some embodiments of the present invention.

FIG. 4C1 is a side view of a portion of perforated light-sheet 401, according to some embodiments of the present invention.

FIG. 4A2 is an end view of a portion of a perforated light-sheet 401' with air scoops 470 and large metal areas 479 adjacent the LEDs 130, according to some embodiments of the present invention.

FIG. 4B2 is a plan view of a portion of perforated light-sheet 401', according to some embodiments of the present invention.

FIG. 4C2 is a side view of a portion of perforated light-sheet 401', according to some embodiments of the present invention.

FIG. 4D is an end view of a portion of perforated light-sheet 404 with air scoops 470, according to some embodiments of the present invention.

FIG. 4E is a plan view of a portion of perforated light-sheet 404, according to some embodiments of the present invention.

FIG. 4F is a top view of a portion of perforated light-sheet 404, according to some embodiments of the present invention.

FIG. 4G is a cross-section top view of a portion of perforated light-sheet assembly 407 made using two perforated light-sheets 408 with varied-sized air scoops 471-475, according to some embodiments of the present invention.

FIG. 4H is a perspective view of a portion of perforated light-sheet assembly 409 with same-sized air scoops 470, according to some embodiments of the present invention.

FIG. 5 is a perspective view of a portion of perforated light-sheet assembly 500, according to some embodiments of the present invention.

DETAILED DESCRIPTION OF THE INVENTION

Figure 1E:
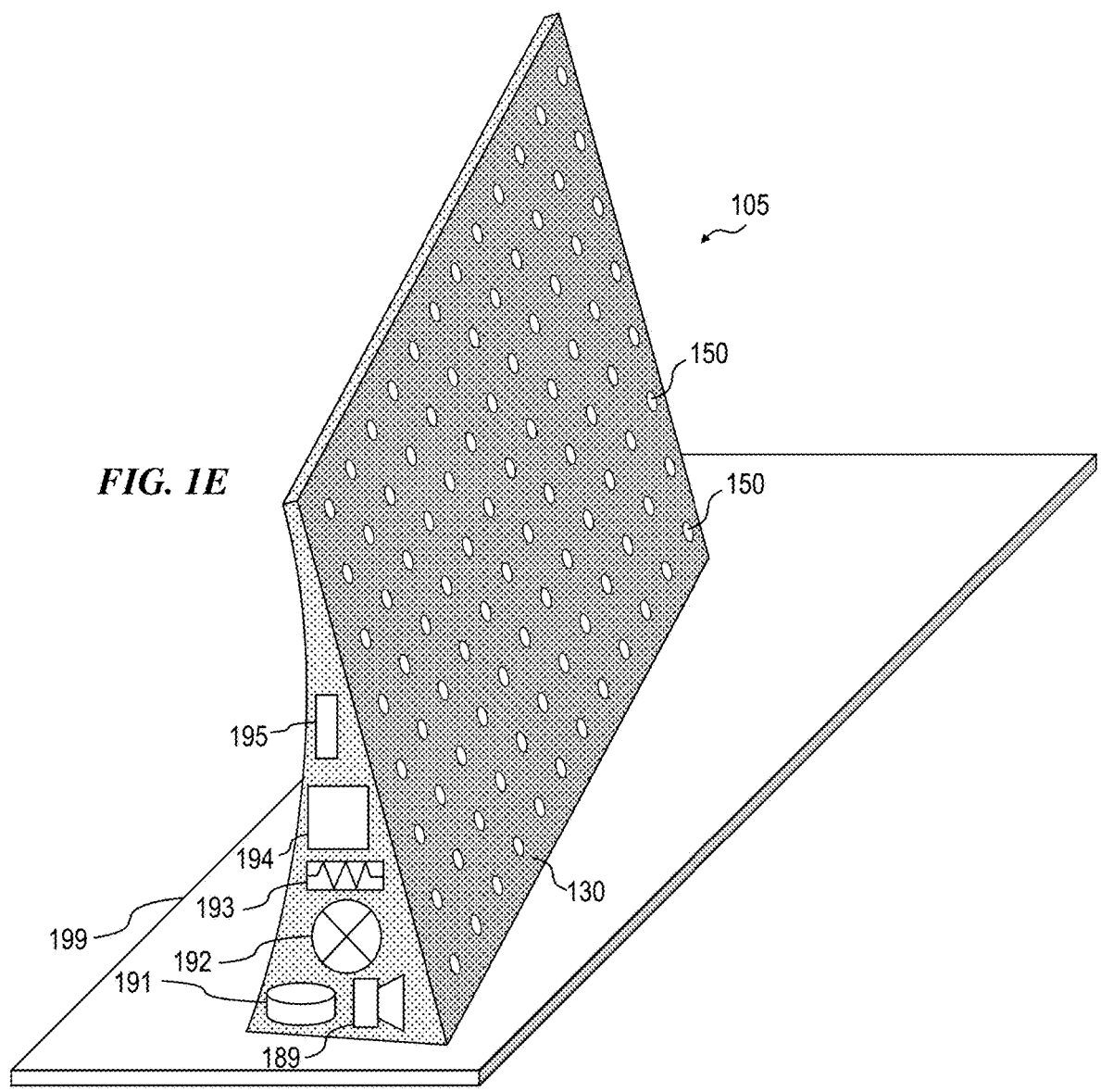
FIG. 1E is an orthographic view of a lighted gas-delivery therapy system 105 utilizing a perforated light-sheet 130, according to some embodiments of the present invention.

Although the following detailed description contains many specifics for the purpose of illustration, a person of ordinary skill in the art will appreciate that many variations and alterations to the following details are within the scope of the invention. Specific examples are used to illustrate particular embodiments; however, the invention described in the claims is not intended to be limited to only these examples, but rather includes the full scope of the attached claims. Accordingly, the following preferred embodiments of the invention are set forth without any loss of generality to, and without imposing limitations upon the claimed invention. Further, in the following detailed description of the preferred embodiments, reference is made to the accompanying drawings that form a part hereof, and in which are shown by way of illustration specific embodiments in which the invention may be practiced. It is understood that other embodiments may be utilized and structural changes may be made without departing from the scope of the present invention.

It is specifically contemplated that the present invention includes embodiments having combinations and subcombinations of the various embodiments and features that are individually described herein (i.e., rather than listing every combinatorial of the elements, this specification includes descriptions of representative embodiments and contemplates embodiments that include some of the features from one embodiment combined with some of the features of another embodiment, including embodiments that include some of the features from one embodiment combined with some of the features of embodiments described in the patents and application publications incorporated by reference in the present application). Further, some embodiments include fewer than all the components described as part of any one of the embodiments described herein.

The leading digit(s) of reference numbers appearing in the Figures generally corresponds to the Figure number in which that component is first introduced, such that the same reference number is used throughout to refer to an identical component which appears in multiple Figures. Signals and connections may be referred to by the same reference number or label, and the actual meaning will be clear from its use in the context of the description.

FIG. 1A is a plan view of a portion of a perforated light sheet 101, according to some embodiments of the present invention. In some embodiments, light sheet 101 includes a plurality of perforations 150 and a plurality of LEDs 130 mounted on junctions of series conductors 125, which are connected to one another between rows of LEDs 130 by parallel conductors 135, wherein a polymer substrate 124 is visible in the rectangular space with rounded corners between each adjacent pair of series conductors 125 and each adjacent pair of parallel conductors 135. In some embodiments (as shown in FIG. 4A1 herein, and also shown in P.C.T. Patent Application Publication WO/2018/089955, which is incorporated herein by reference), each LED is mounted right next to a junction 138 between two parallel conductor and forming a series-connected plurality of sets of parallel-connected LEDs, in order for each LED to be as close as possible to the larger metal area (e.g., metal areas 479 of FIG. 4A1) adjacent the junction 138 in order to better spread the heat from the operating LEDs to the horizontal parallel conductors 135 to the left and right of the junction and to the vertical series-connected conductors 125 (above the junction and below the LED for LEDs in the upper half of perforated light sheet 101, and below the junction 138 and above the LED 130 for LEDs in the lower half of perforated light sheet 101). In some embodiments (not shown here but shown in P.C.T. Patent Application Publication WO/2018/089955, which is incorporated herein by reference), each row 110 has the same height, whereas two middle rows 111 are of a smaller height, in order that all LEDs are evenly spaced vertically and the LEDs on the upper-edge row and the lower-edge row are closer to the top and bottom conductors 121 and 122. In some embodiments, top conductor 121 is the DC power-supply conductor and bottom conductor 122 is the DC ground conductor. In some embodiments, polymer substrate 124 extends slightly beyond the outer edge of the top and bottom conductors 121 and 122, and of the left-most and right-most series conductors 125. In some embodiments, rounded or circular holes 150 are provided between each adjacent pair of series conductors 125 and each adjacent pair of parallel conductors 135. In some embodiments, round holes are used and the junctions 138 between series conductors 125 and parallel conductors 135 are of larger area for increased physical panel strength and better heat spreading to keep the temperature rise smaller.

FIG. 1B1 is a cross-section view of a portion of a plenum cartridge 102A (also sometimes called a gas-delivery plant-light assembly or fixture), showing a cross-section view of two oppositely facing perforated light-sheets 101 along section line 1B1 of FIG. 1A, according to some embodiments of the present invention. In some embodiments, each perforated light-sheet 101 includes a perforated substrate 136, a plurality of LEDs 130 connected to conductors 123. In some embodiments, a supply of gas 161 is forced into the plenum cartridge 102A through duct or pipe 160 and exits both sides to the vegetative or crop plants through opening 150. In some embodiments, insulating connectors 139 (e.g., a polymer filament with knobbed ends or the like) are used to minimize ballooning of the light sheets that would otherwise occur due to the gas 161 being pushed through the skinny duct plenum cartridge 102A. In some embodiments, a clear polymer cover sheet (not shown in this Figure, but such as shown as sheet 137 of FIG. 1B2) is used on the outer surfaces of light sheets 101.

FIG. 1B2 is a top cross-sectional view of a portion of assembled gas-delivery plant light apparatus 102B having a clear polymer cover 137 and a plurality of push-pin type air-pore devices 156, according to some embodiments of the present invention. In some embodiments, hollow air-pore devices 156 (such as a cylindrical polymer tube) are formed or flared at their inner and outer ends to have a larger diameter outside the clear polymer cover 137 and inside the perforations of perforated light-sheet 101 in order to form air pores with through-hole passageways that function to emit/deliver gas 151 to the plant crops (see FIG. 1D, plants 181); the end flares of air-pore devices 156 also function to hold together the parts of plant light apparatus 102B. In some embodiments, insulating connectors 139 (e.g., a polymer filament with knobbed ends or the like) are used to minimize ballooning of the light sheets that would otherwise occur due to the gas 161 being pushed through the skinny duct plenum cartridge 102B. In some embodiments, insulating connectors 139 connect the outer clear polymer cover 137 to the center support sheet 190 alternately on each surface, while in other embodiments, insulating connectors 139 connect the outer clear polymer cover 137 on one side to the outer clear polymer cover 137 on the opposite side.

Figure 3:
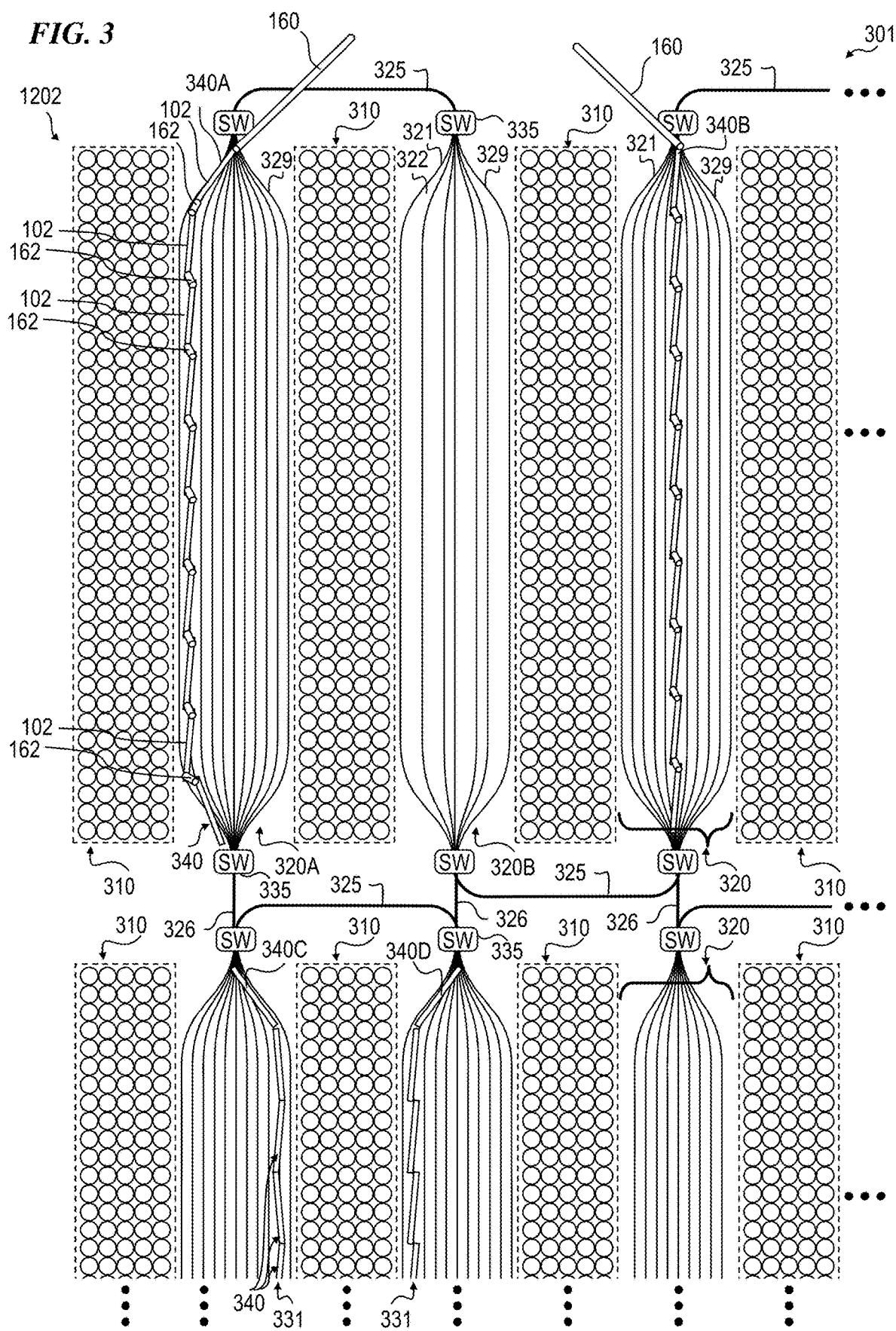

FIG. 1B3 is a top cross-sectional view of a portion of plant light apparatus 102C having a clear polymer cover 137 and a plurality of air-pore devices 156 having T-shaped air dispersers 173, according to some embodiments of the present invention. In some embodiments, T-shaped air dispersers 173 function to spread the gas 151 to the sides of the pores 150 through air-pore devices 156 such that crop plants get air pushing the leaf structures sideways, particularly when the structure of assembled plant light apparatus 102C is combined with an oscillating or swinging assembled plant light apparatus 107 such as shown in FIG. 1G and FIG. 1H1.

FIG. 1B4 is a top cross-sectional view of a portion of gas-delivery plant light apparatus 102D having a clear polymer cover 137 and a plurality of air-pore devices 156 having flapper air dispersers 174, according to some embodiments of the present invention. In some embodiments, flapper air dispersers 174 are flexible polymer structures that are inherently unstable such that they physically flap and oscillate back and forth to provide oscillating gas flow (of a gas such as air), when gas is pumped through gas-delivery plant light apparatus 102D. In some preferred embodiments, the flapper air dispersers 174 are designed such that the oscillation is about 600 hertz (or, in other embodiments, in a range from 300 to 900 hertz, in a range of about 500 to about 700 hertz, in a range of about 400 to about 800 hertz, or in another suitable range), which is thought by some to promote plant pollination.

Figure 5:
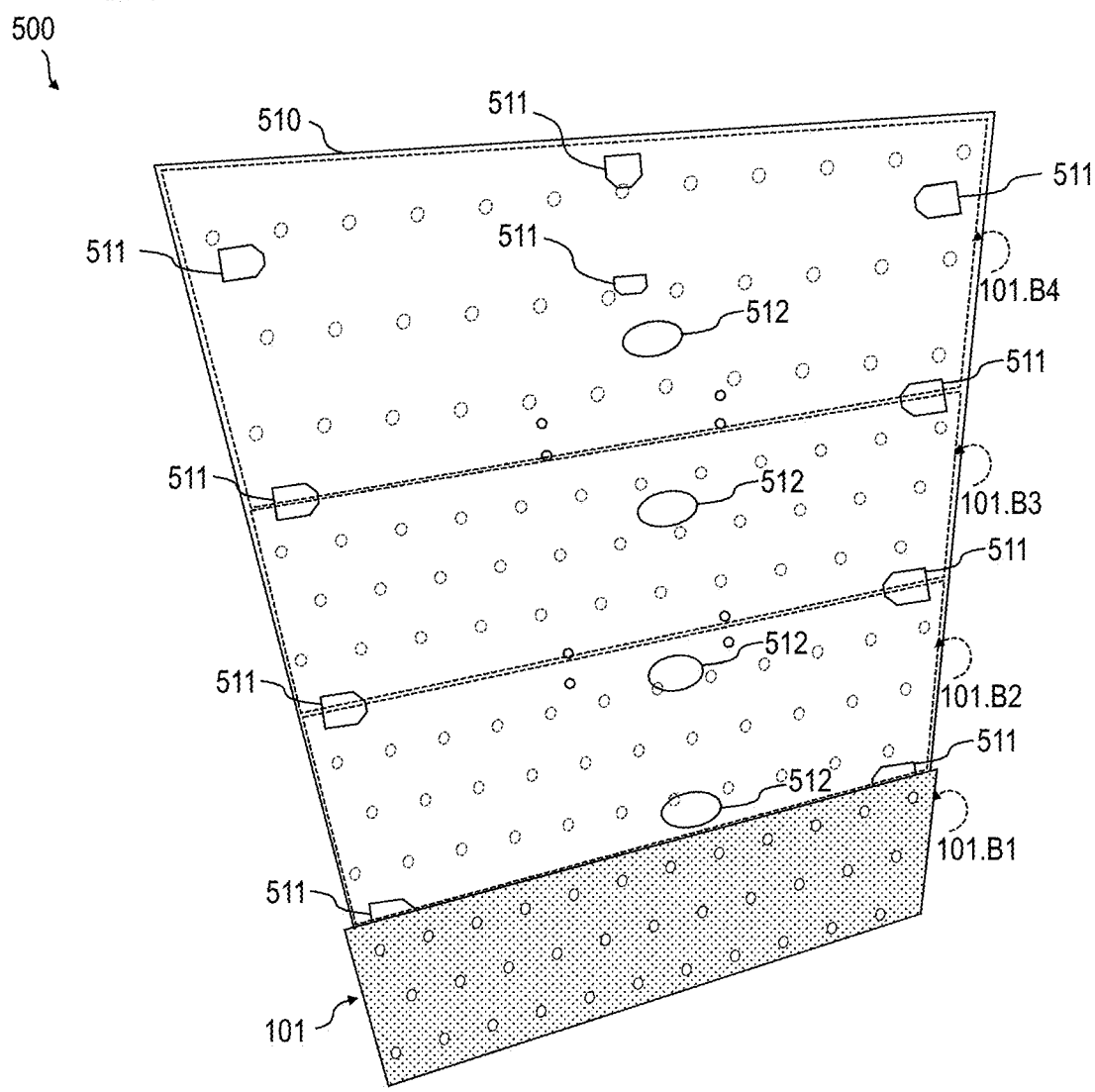

FIG. 1B5 is a top cross-sectional view of a portion of gas-delivery plant light apparatus 102E having a clear polymer cover 137 and a plurality of air-pore devices 156 having spiral-shaped air dispersers 175, according to some embodiments of the present invention.

FIG. 1B6 is a top cross-sectional view of a portion of gas-delivery plant light apparatus 102E having a clear polymer cover 137 and a plurality of air-pore devices 156 having flapper air dispersers 176 on a mover device 189 according to some embodiments of the present invention. In some embodiments, mover device 189 oscillates left and right, thus moving flapper air dispersers 176 back and forth using the pore sides as fulcrum points.

FIG. 1B7 is a top cross-sectional view of a portion of assembled gas-delivery plant light apparatus 102G having a clear polymer cover 137, a plurality of short air-pore devices 156 connecting the clear polymer cover 137 to the perforated plant light sheet 101, and a plurality of long air-pore devices 158 connecting the clear polymer cover 137 to the perforated center sheet 190, according to some embodiments of the present invention. In some such embodiments, the long air-pore devices help minimize and/or prevent ballooning of the plenum shape as gas 161 is forced into gas-delivery plant light apparatus 102G.

FIG. 1B8 is a schematic top cross-sectional view of a skinny gas-delivery plant light system 104 having a gas-movement unit 192 (such as a gas pump, fan or other actuator) and an assembled gas-delivery plant light apparatus 102, according to some embodiments of the present invention. In some embodiments, gas-delivery plant light system 104 includes an LED power supply 187, an air-pulsing device 188 (such as a periodically activated piston or the like) to selectively pulse the air supply from time to time to agitate the leaves of the crop plants, an audio transducer 189 that outputs an audio signal (e.g., in some embodiments, 600 Hz) to help the plants self-pollinate, and/or a gas-movement unit 192. In some embodiments, gas-movement unit 192 is also (or alternatively instead of air-pulsing device 188) used to periodically pulse the gas and/or air supply delivered to gas-delivery plant light apparatus 102. In some embodiments, gas-movement unit 192 is also (or alternatively instead of audio transducer 189) used to periodically or continuously supply an audio signal into the gas delivered to gas-delivery plant light apparatus 102.

In some embodiments, any one or more of the assembled gas-delivery plant light apparatuses 102A through 102G of FIGS. 1B1-1B7 are combined to form a gas-delivery plant light apparatus 102 such as shown in FIG. 1B8, FIG. 1C and FIG. 1D or with swinging gas-delivery plant light apparatus 107 such as shown in FIG. 1G and FIG. 1H1.

FIG. 1C is an orthographic view of assembled gas-delivery plant light apparatus 102, according to some embodiments of the present invention. In some embodiments, gas-delivery plant light apparatus 102 includes a plurality of perforated light sheets 101 (e.g., one or more facing in two opposite directions), each perforated light sheet 101 having a plurality of LEDs 130 and holes 150. In some embodiments, gas-delivery plant light apparatus 102 includes a gas-delivery duct 160 and a plurality of rollers 170 from which gas-delivery plant light apparatus 102 is hung and moved along overhead tracks (as shown in FIG. 1H1 reference number 176). In some embodiments, each gas-delivery plant light apparatus 102 is implemented as one or more of plant light apparatuses 102A through 102G of FIGS. 1B1-1B7, respectively, for example 102A of FIG. 1B1 or 102B of FIG. 1B2. In some embodiments, gas-delivery plant light apparatus 102 is implemented using a plurality of the same type selected from plant light apparatuses 102A through 102G of FIGS. 1B1-1B7, while in other embodiments, different ones of plant light apparatuses 102A through 102G of FIGS. 1B1-1B7 are combined to implement gas-delivery plant light apparatus 102 of FIG. 1C.

In some embodiments, the thickness of gas-delivery plant light apparatus 102 is made thin enough, and the height and width of plant light apparatus 102 sufficiently tall and wide, in order to locate pot-holder systems 180 very close together to maximize the number of plants in a given volume. For example, in some embodiments, each gas-delivery plant light apparatus 102 has a thickness of no more than 2 cm (about 0.8 inches), while in other embodiments, the thickness is no more than 4 cm, no more than 6 cm, no more than 8 cm or no more than 10 cm (about 2.5 inches). In other embodiments, gas-delivery plant light apparatus 102 has a thickness of no more than 15 cm, a thickness of no more than 20 cm, a thickness of no more than 30 cm, a thickness of no more than 40 cm, or a thickness of no more than 50 cm (about 18 inches). In some preferred embodiments, the thickness of gas-delivery plant light apparatus 102 is no more than 25 cm (about 10 inches). In some embodiments, the height of each gas-delivery plant light apparatus 102 is at least 2 meters (about 6.5 feet tall), with a width of at least 1.22 meters (about 4 feet wide). In some other embodiments, the height of each gas-delivery plant light apparatus 102 is at least 3 meters, at least 4 meters, at least 5 meters, or at least 6.1 meters (about 20 feet tall). In some other embodiments, the width of each gas-delivery plant light apparatus 102 is at least 2 meters, at least 3 meters (about 10 feet wide), at least 4 meters, at least 5 meters, or at least 6.1 meters (about 20 feet wide).

Of course, different widths and heights can be combined for a given application of gas-delivery plant light apparatus 102, such as a height of about 2.44 meters (about 8 feet tall) and a width of about 1.22 meters (about 4 feet wide). Five such 4-foot-wide gas-delivery plant light apparatus 102 would be placed between and be used to illuminate two parallel walls of pot-holder systems 180 that are each about 12.2 meters long (about 40 feet long), wherein the five gas-delivery plant light apparatus 102 would be moved sideways to different locations every 12 hours to alternately illuminate different sections of the 40-foot-long wall of pot-holder systems 180. In that way, each plant would receive 12 hours of light during each 24-hour period.

In some embodiments, the thickness of each of the pot-holder systems 180 is made thin enough, and tall and wide, in order to locate the pot-holder systems 180 very close together to maximize the number of plants in a given volume. For example, in some embodiments, each pot-holder system 180 has a thickness of no more than 20 cm (about 8 inches), while in other embodiments, the thickness is no more than 40 cm, no more than 60 cm, no more than 80 cm or no more than 100 cm (about 25 inches). In some preferred embodiments, the thickness of pot-holder system 180 is no more than 25 cm (about 10 inches), and a plurality of pot-holder systems 180 are located parallel to one another at a center-to-center spacing of about 30 to 35 cm (about 12 to 14 inches), with one or more gas-delivery plant light apparatus 102 located between each pair of crop plant walls to be moved sideways to different locations every 12 hours to alternately illuminate different sections of the walls of pot-holder systems 180. In that way, each plant receives 12 hours of light and 12 hours of darkness during each 24-hour period.

FIG. 1D is an orthographic view of a plant-growth system 103 utilizing a plurality of assembled plant light apparatuses 102, each located between a respective pair of walls of pot-holder systems 180, according to some embodiments of the present invention. In some embodiments, plant-growth system 103 includes a plurality of holder systems 180 each having a plurality of plant holders or pots held or formed horizontally or at an angle between horizontal and vertical, oriented on each wall, and the plants 181 grow generally horizontally from each pot in the space between the pot and the ducted light panel systems 102 adjacent the pot. In other embodiments, the pots are oriented horizontally with the plants growing initially sideways (horizontally) and then growing upward and/or downward vertically (for example, herbs or tomato vines) over and along the sides of the pot-holder systems 180.

FIG. 1E is an orthographic view of a lighted desktop gas-delivery therapy system 105 utilizing a perforated light-sheet 130, according to some embodiments of the present invention. In some embodiments, lighted desktop gas-delivery therapy system 105 (placed on desktop 199) includes a source of aromatic and/or pharmaceutical chemicals 191, a fan, pump or other gas-moving device 192, a thermoelectric or other temperature-control device 193, an oxygen-enhancing device 194 (such as a source of compressed oxygen gas or an oxygen-enhancing apparatus as are well known in the art), and a controller 195 that controls devices 191, 192, 193, and/or 194 and/or the LEDs 130. In some embodiments, lighted desktop gas-delivery therapy system 105 is configured to be useful in the treatment of seasonal affective disorder (SAD).

In some embodiments, the spectrum of the LEDs 130 of lighted desktop gas-delivery therapy system 105 is adjustable and controlled by the user and/or a timer such that more blue (shorter-wavelength) light is emitted in the morning (or upon the user waking after sleep) by activating and/or providing a greater duty cycle to blue (e.g., about 440 nm to 470 nm wavelength) LEDs and/or LEDs that emit a cool-white light (e.g., having a color temperature of greater than 5000K) to make the user more alert for the day ahead. Conversely, the spectrum of the LEDs 130 is controlled by the user and/or a timer to emit mostly red (longer-wavelength) light in the evening in order to help the user get sleepy and ready for a night of restful sleep.

Figure 1F:
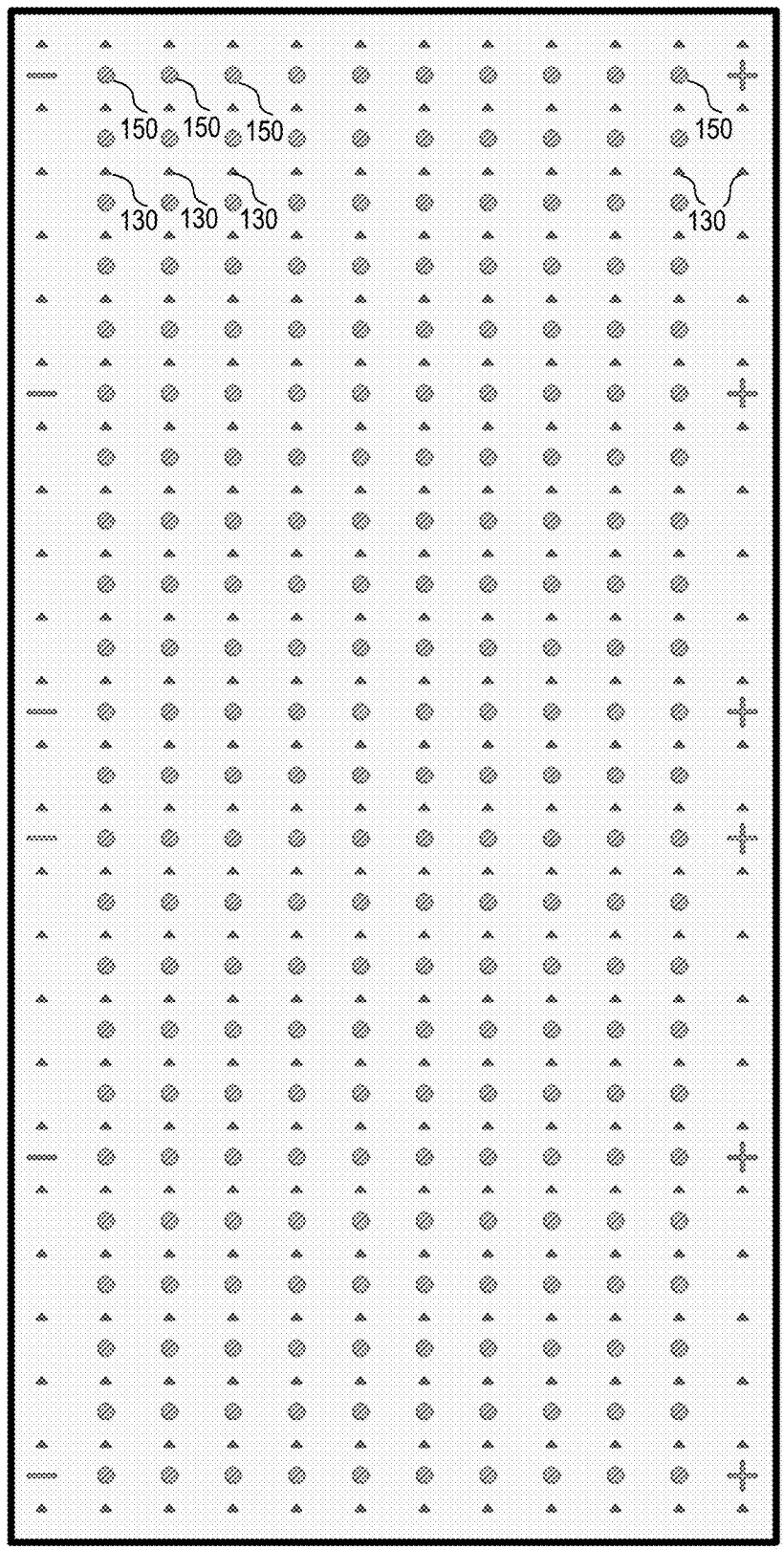
FIG. 1F is a plan view of a perforated light-sheet system 106 with small circular holes, according to some embodiments of the present invention.

FIG. 1F is a plan view of a perforated light-sheet system 106 with an array of small circular holes 150 distributed among an array of LEDs 130, according to some embodiments of the present invention. In some embodiments, perforated light-sheet system 106 can be used for making the gas-delivery light-panel systems 102, or as a starting part for further processing into any suitable one of the other perforated light sheets (such as 101) or parts for skinny gas-delivery lighting fixtures (such as 102, 102A through 102G, 105, 103A, 103b, 103c, 401, 402, 404, 407 and the like).

FIG. 1G is an orthographic view of a swinging assembled plant light apparatus 107, according to some embodiments of the present invention. In some embodiments, a rotary motor 168 drives a rotating camshaft 167 connected to a connecting rod 169, in order to move gas-delivery plant light systems 102 in an oscillating motion 181. In some embodiments, gas-delivery plant light systems 102 is hung from pendulum-like connectors 169, such that when moved back and forth along a mostly width-wise direction by motor 168, camshaft 167 and connecting rod 169, the gas that is emerging through-holes (pores) 150 is moved back-and-forth across the adjacent crop plants. In some embodiments, back-and-forth plant-light apparatus 107 is used to agitate the leaves of the crop plants, in addition to (or instead of) air-pulsing device 188 and/or a gas-movement unit 192 of plant light system 104 shown in FIG. 1B8.

FIG. 1H1 is an orthographic view of a plant-growth system 108 utilizing a plurality of swinging gas-delivery plant light apparatuses 107 on both sides of a wall of plants 181 growing from pots or other plant holders of a wall pot-holder system 180, according to some embodiments of the present invention. In some embodiments, a repeating series of parallel walls of pot-holder systems 180 have a plurality of gas-delivery plant light apparatuses 107 located therebetween, and movable along a length direction 182 (e.g., in some embodiments, on a 12-hour on, 12-hour off schedule such that each group of plants gets 12 hours of light and gas delivery and 12 hours of dark. In some embodiments, a hanger 179 is supported by rollers 170 that roll along tracks 176.

FIG. 1H2 is an orthographic view of a small sub-portion of pot-holder system 180, according to some embodiments of the present invention. In some embodiments, pot-holder system 180 includes a light-weight sheet of material 196, such as sheet metal (e.g., steel or aluminum) or polymer (such as a polypropylene film or extruded polystyrene) or fabric, a plurality of "pots" 197 such as hollow cylinders of polypropylene film, recycled fabric or other suitable material, wherein each pot 197 is stuffed with a water-holding material or mixture 198 (such as fiberglass "wool" combined with water-retaining plant gel (such as plant gel soil alternative such as available from www.seedman.com/plant-ge.htm, or Miracle-Gro® Water Storing Crystals available at many retail outlets)). In some embodiments, "pots" 197 are vacuum-formed as pockets in a polypropylene film sheet 196, wherein alternating "pots" 197 are vacuum-formed as cylindrical (or other suitable hollow prism shape) pockets on alternate sides of polypropylene film sheet 196 such as shown in FIG. 1H3.

FIG. 1H3 is an orthographic view of a small sub-portion of plant-holder system 180', according to some embodiments of the present invention. In some such embodiments, the support sheet 196' (such as a thin sheet or film of polypropylene, aluminum, non-woven fabric, or the like) has the first subpopulation of cup-shaped pockets 197' (called the far-side pockets) with their convex surfaces extending outward from the far surface of support sheet 196', while the other second subpopulation of cup-shaped pockets 197" (called the near-side pockets) have their convex surfaces extending outward from the opposite (near-side) surface of support sheet 196'. In some embodiments, cup-shaped pockets 197" and cup-shaped pockets 197' are made by heating support sheet 196' and vacuum forming the desired shape. In some embodiments, the central axis of each cup-shaped pocket 197" and 197' is perpendicular to the plane of support sheet 196' and the fill material 198 is stiff enough to hold the plants in place while they grow. In other embodiments, the central axis of each cup-shaped pocket 197" is downward sloping toward the closed deep end of each pocket (such as shown in FIG. 1H4) to provide improved support for the rooting material 198 and the plants 181. This solution provides a denser (thinner) plant-holder system 180' since the horizontal extent of the crop plants 181 growing towards the right from far-side pockets 197' extend only from the plane of the near-side surface of sheet 196' and are in the near-side volume of space also occupied by the near-side pockets 197", and conversely the horizontal extent of the crop plants 181 growing towards the left from near-side pockets 197" extend only from the plane of the near-side surface of sheet 196' and are in the near-side volume of space also occupied by the far-side pockets 197'.

FIG. 1H4 is an orthographic view of a small sub-portion of plant-holder system 180", according to some embodiments of the present invention. In some such embodiments, the central axis of each cup-shaped pocket 197" is downward sloping toward the closed deep end of each pocket (such as shown in FIG. 1H4) to provide improved support for the rooting material/soil substitute 198 and the plants 181.

FIG. 1i is a plan view of an enclosed plant-growth container apparatus 990 that includes an enclosure 991 having a plurality of plant-growth systems 109 therein, and a door 992, according to some embodiments of the present invention.

FIG. 1J is an orthographic view of a plant-growth system 109 utilizing a plurality of swinging plant light apparatuses 107 and a plurality of movable plant walls 185, according to some embodiments of the present invention.

TABLE 1

External measurements for some embodiments of container 990

| Type | Length | Width | Standard Height | High-Cube Height |
|---|---|---|---|---|
| 20 ft | 20'(6.06 m) | 8'(2.44 m) | 8' 6"(2.59 m) | 9' 6"(2.89 m) |
| 25 ft | 25'(7.58 m) | 8'(2.44 m) | 8' 6"(2.59 m) | 9' 6"(2.89 m) |
| 30 ft | 30'(9.12 m) | 8'(2.44 m) | 8' 6"(2.59 m) | 9' 6"(2.89 m) |
| 40 ft | 40'(12.19 m) | 8'(2.44 m) | 8' 6"(2.59 m) | 9' 6"(2.89 m) |
| 45 ft | 45'(13.72 m) | 8'(2.44 m) | 8' 6"(2.59 m) | 9' 6"(2.89 m) |

TABLE 2

Internal measurements for some embodiments of container 990

| Type | Length | Width | Standard Height | High-Cube Height |
|---|---|---|---|---|
| 20 ft | 19' 3"(5.87 m) | 7' 8"(2.33 m) | 7' 9"(2.35 m) | 8' 9"(2.65 m) |
| 25 ft | 24' 4"(7.43 m) | 7' 8"(2.33 m) | 7' 9"(2.35 m) | 8' 9"(2.65 m) |
| 30 ft | 29' 4"(8.93 m) | 7' 8"(2.33 m) | 7' 9"(2.35 m) | 8' 9"(2.65 m) |
| 40 ft | 39' 5" (12.00 m) | 7' 8"(2.33 m) | 7' 9"(2.35 m) | 8' 9"(2.65 m) |
| 45 ft | 44' 4" (13.51 m) | 7' 8"(2.33 m) | 7' 9"(2.35 m) | 8' 9"(2.65 m) |

Figure 2A:
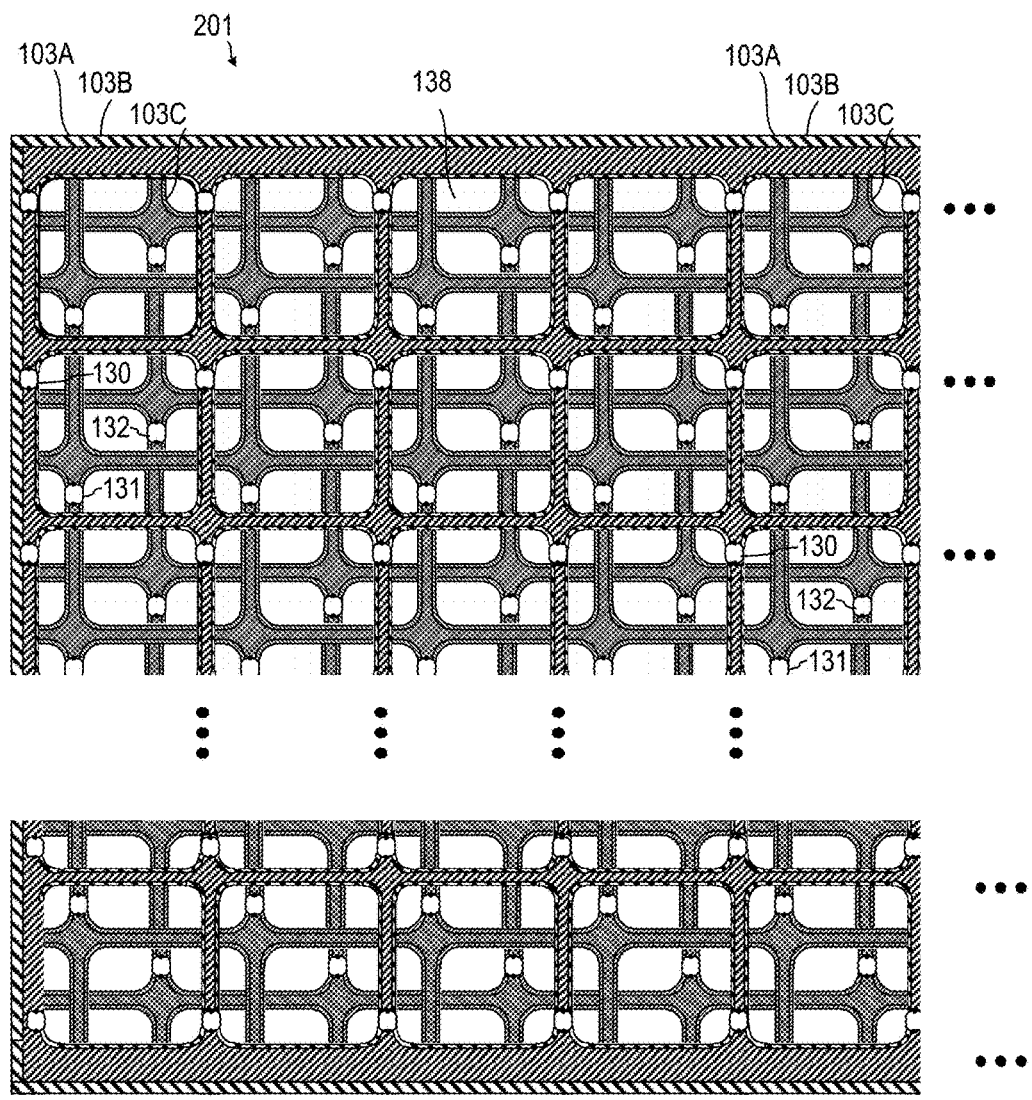
FIG. 2A is a plan view of a perforated light-sheet system 201 with small circular holes, according to some embodiments of the present invention.

FIG. 2A is a plan view of a portion of a stacked perforated light-sheet system 201 with a plurality of layers of perforated light-sheet 103, according to some embodiments of the present invention. In some embodiments, the outermost layer 103A is stacked on a middle layer 103B and innermost layer 103C. In other embodiments, other numbers of layers are used. In some embodiments, each different layer includes a plurality of LEDs having an overall different spectrum than the spectra of other layers. In some embodiments, this allows the intensity of light of each spectrum to be controlled independent of the other spectra (e.g., by using different duty cycles of pulse-width modulation (PWM) or different current amounts), while each light sheet 103 needs only a single layer of conductor, thus reducing costs. In other embodiments, two or more of the layers have the same or substantially similar spectra. In some embodiments, such a multi-layer multi-color stacked perforated light-sheet system 201 is used in a SAD-light- and aromatherapy-therapy system such as system 105 shown in FIG. 1E. In other embodiments, rather than large holes 138, the substrate is made of a transparent polymer and smaller holes are provided.

Figure 2B:
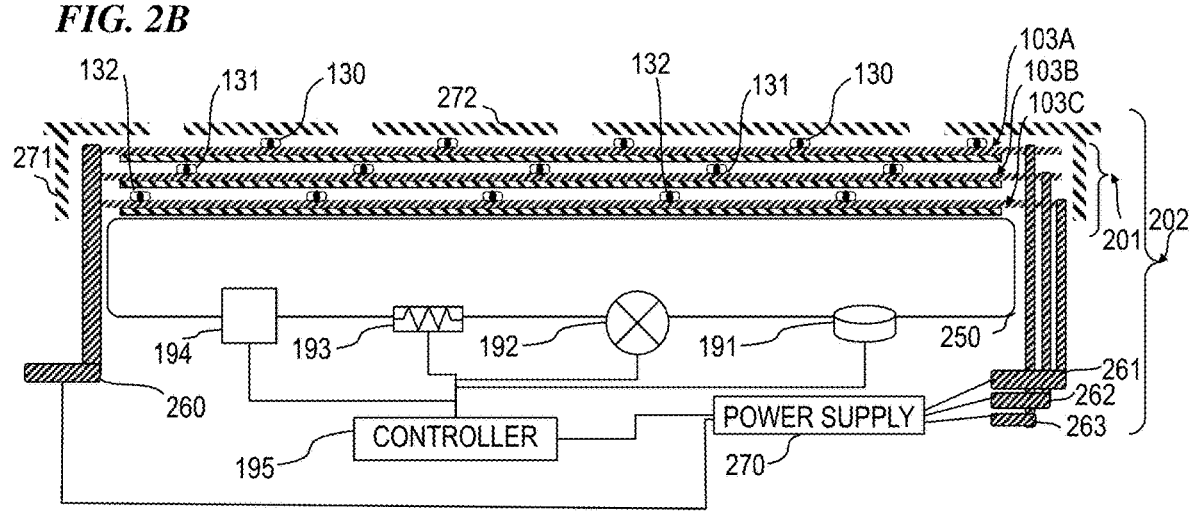
FIG. 2B is a cross-section block diagram of a portion of a SAD-light- and aromatherapy-therapy perforated light-sheet system 202, according to some embodiments of the present invention.

FIG. 2B is a cross-section block diagram of a portion of a SAD-light- and aromatherapy-therapy perforated light-sheet system 202, according to some embodiments of the present invention. In some embodiments, a stacked perforated light-sheet system 201 includes a plurality of perforated light sheets (e.g., in some embodiments, 103A, 103B, 103C). In some embodiments, system 202 includes a common insulated conductor 260 used to supply power to all three light sheets 103A, 103B, and 103C. In some embodiments, system 202 further includes individual conductors 261, 262, and 263 that are individually connected to their own respective sheet (e.g., in some embodiments, conductor 261 is connected to sheet 103A, conductor 262 is connected to sheet 103B, and conductor 263 is connected to sheet 103C) with power supply 270 under control of controller 195 in order to provide sheet-specific control of amount of current, pulse-width modulation, and/or other suitable signal control, in order to control brightness (amount of light) and/or color spectrum (which wavelengths and how much of each wavelengths are emitted) and/or time-of-day or time-of week or season to use for each spectrum and/or brightness.

FIG. 3 is a top view of plant light system 301, with a plurality of parallel tracks for variable light-to-plant spacings, according to some embodiments of the present invention. In some embodiments, one or more hanging chained (or hinged) and ducted light panel systems 331 each having a string of gas-pipe-connected and electrical-power-connected gas-delivery light panels or systems 340 (in some embodiments, implemented by gas-delivery plant light systems 102 as shown in FIG. 1C and FIG. 1D) are movable by sliding the ducted light panel systems 331 in an end-to-end direction from any of a plurality of tracks 321, 322, . . . 329 of one set of parallel tracks 320 (e.g., 320A) to any of a plurality of tracks 321, 322, . . . 329 of another set of parallel tracks 320 (e.g., 320B). The selectable one of the parallel tracks allows a desired spacing to the adjacent set of pot-holder systems 180 (such as shown in FIG. 1H1 or FIG. 1J) or shelves 310 of pots, wherein a plurality of plant holders or pots are formed or positioned horizontally (as shown in FIG. 1H2 and FIG. 1H3) or at an angle between horizontal and vertical oriented (such as shown in FIG. 1H4) or on each shelf and the plants grow horizontally from each pot in the space between the pot and the ducted light panel systems 331 adjacent the pot. In other embodiments, the pots are oriented horizontally with the plants growing initially sideways (horizontally) and then upward and/or downward vertically (for example, tomato vines) over and along the sides of the pot-holder systems 180 or shelves of pots 310. While seven, nine or eleven parallel tracks (321, 322, . . . 329) are shown for each set of tracks 320 in this FIG. 3, other embodiments use other quantities of parallel tracks between adjacent shelf units 310. In some embodiments, each hanging ducted light-sheet panel 340 of a given hanging ducted light panel system 331 is connected to the neighboring hanging light-sheet panels 340 by a common chain along the track from which it is hanging and by a series of inter-panel ducts 162, with one or more ducts 160 supplying gas and electrical conductors supplying electrical power to the set of hanging ducted light panel systems 331. Such chain-and-duct systems generally need the leading edge of a given hanging light panel system 331 to be pulled towards its destination (wherever the light and gas is desired at a given time). In some other embodiments, each hanging ducted light panel system 102 of a given hanging light panel system 331 is connected to the neighboring hanging light-sheet panels by one or more hinges and one or more ducts along the vertical length of the adjacent panels, and each panel is optionally connected at its top to the track currently being used. Such hinged ducted systems allow either the leading edge of a given hanging light panel system 331 to be pulled towards its destination or the trailing panel to be pushed so that the hanging light panel system 331 moves towards the desired destination. In other embodiments, still other systems (such as those various ones used for vertical Venetian blinds) are used.

FIG. 4A1 is an end view of a portion of a perforated light-sheet 401 with air scoops 470 and large metal areas 479 (e.g., of a copper film or plating used as electrical conductor on an insulating substrate 427 as shown in FIG. 4B1 and FIG. 4B2) adjacent the LEDs 130 (LEDs on the opposite side of the substrate, away from the convex side of the scoops 470), according to some embodiments of the present invention. In some embodiments, non-electrically conductive gaps 478 (as shown in FIG. 4B1 and FIG. 4B2) separate adjacent ones of wide large metal areas 479, and a row of parallel-wired LEDs 130 is mounted across each relatively narrow non-electrically conductive gap 478, such that the plurality of rows of parallel-wired LEDs 130 are wired in series between external connector locations at the very top and very bottom ones of the large metal areas 479. In some embodiments, such air scoops 470 allow better and more even air collection and/or air emission from plenum-mounted light sheets. In some embodiments, for some systems in which air is emitted from a supply-air plenum (such as 102A through 102G of FIGS. 1B1 through 1B7, respectively), the scoops 470 extend inward from the outside face in a direction away from the LEDs and the light emission from the outer surfaces, while in some other embodiments of systems (not shown here), in which air is collected into a return-air plenum, the scoops extend outward from the same side as the LEDs and the side of light emission.

In some embodiments, the metal areas 479 form more than half the area of perforated light-sheet 401, which provides a low-resistance electrical conductor as well as a heat conductor for spreading the heat from the LEDs 130 to avoid high-temperature hot spots that can damage adjacent crop plants, thus allowing perforated light-sheet 401 to be mounted closer to the crop plants, which can increase the intensity of light onto the crop plants and make for a more concentrated grow house (one with more plants per unit volume) thus lowering the cost for facilities that enclose the plants and gas-delivery lighting systems as described herein.

FIG. 4B1 is a plan view of a portion of perforated light-sheet 401 with air scoops 470, according to some embodiments of the present invention. In some embodiments, holes 426 occupy a small portion of each space between each adjacent pair of series conductors 425 and each adjacent pair of parallel conductors 435 (see FIG. 4B2 for an example indication of these conductors).

FIG. 4C1 is a side view of a portion of perforated light-sheet 401 with air scoops 470 that are all of the same height, according to some embodiments of the present invention.

FIG. 4A2 is an end view of a portion of a perforated light-sheet 402 with air scoops 470 and relatively small metal areas 479' adjacent the LEDs 430 (LEDs on the same side of the substrate as the convex side of the scoops 470), according to some embodiments of the present invention. In some embodiments, relatively large areas of non-electrically conductive substrate 427 connect gaps 478' that separate adjacent ones of narrow metal areas 479', and a row of parallel-wired LEDs 430 is mounted across each non-electrically conductive gap 478', such that the plurality of rows of parallel-wired LEDs 430 are wired in series between external connector locations at the very top and very bottom ones of the metal areas 479'.

FIG. 4B2 is a plan view of a portion of perforated light-sheet 402, according to some embodiments of the present invention.

FIG. 4C2 is a side view of a portion of perforated light-sheet 402, according to some embodiments of the present invention.

FIG. 4D is an end view of a portion of perforated light-sheet 404 with air scoops 470, according to some embodiments of the present invention. In some embodiments, such air scoops allow better and more even air collection and/or air emission from plenum-mounted light sheets. For systems in which air is emitted from a supply-air plenum, the scoops extend outward from the side away from the LEDs and the light emission, while in some embodiments of systems in which air is collected into a return-air plenum, the scoops extend outward from the same side as the LEDs and the side of light emission.

FIG. 4E is a plan view of a portion of perforated light-sheet 404, with air scoops 470, according to some embodiments of the present invention.

FIG. 4F is a top view of a portion of perforated light-sheet 404, according to some embodiments of the present invention.

FIG. 4G is a cross-section top view of a portion of perforated light-sheet assembly 407 made using two perforated light-sheets 408 with varied-sized air scoops 471, 472, . . . -475, according to some embodiments of the present invention. In some embodiments, gas-delivery plenum 407 uses perforated light-sheets 409 with air scoops 471, 472, .

. . . -475 (e.g., in some embodiments, 471, 472, 473, 474, and 475) that have a plurality of different heights, according to some embodiments of the present invention. In some embodiments, the different heights of air scoops 471, air scoops 472, air scoops 473, air scoops 474, and air scoops 475 allow better control of air flow from a plenum and thus more even flow and velocity.

FIG. 4H is a perspective view of a portion of perforated light-sheet assembly 409 with same-sized air scoops 470, according to some embodiments of the present invention.

Some embodiments of the present invention include a stacked perforated scooped light-sheet system (such as shown in FIG. 2B) with a perforated light-sheet 409 with air scoops 470 and one or more layers of perforated light-sheet 103A, 103B and/or 103C, according to some embodiments of the present invention. In some embodiments, the scooped layer 409 (with scoops formed inward (away from the LEDs) or outward (towards the side with LEDs), as the case may be) is stacked on one or more regular perforated light sheets 103A, 103B, 103C to form a stacked perforated scooped light-sheet system. In some embodiments, different layers have different spectra, different LED densities (quantities of LEDs per unit area), and/or different PWM (pulse-width modulation) duty cycles or current amounts in order to vary the intensity, proportion or amount of light of each spectrum of the different layers.

FIG. 5 is a perspective partially cut-away view of a portion of perforated gas-delivery light-sheet assembly 500, according to some embodiments of the present invention. In some embodiments, perforated gas-delivery light-sheet assembly 500 includes a central support sheet 510 (e.g., in some embodiments, galvanized or stainless steel) having a plurality of through-holes 512 that allow gas to pass through the central support sheet 510 to exit through perforations 150 in the LED light sheets 101 on the front side and back side of perforated gas-delivery light-sheet assembly 500, and a plurality of support stand-offs 511 that support a plurality of LED light sheets 101, each spaced slightly apart from central support sheet 510 (e.g., in some embodiments, at a horizontal distance of between about 0.5 cm to about 2.5 cm; while in other embodiments, the horizontal spacing is in a range between about 0.1 cm to about 10 cm or larger). In this FIG. 5, four backside LED light sheets 101.B1-101.B4 are shown, indicated in dotted lines, stacked edge-to-edge up the back side of central support sheet 510, and a single frontside LED light sheet 101, with LEDs 130 and perforations 150, is indicated in solid lines (three other frontside LED light sheets 101 would normally also be attached edge-to-edge vertically, relative to one another, above the single frontside LED light sheet 101 shown here), and appropriate gas supply lines and electrical power and control lines would be used, such as shown in FIG. 1B8 described above. In some embodiments, perforated gas-delivery light-sheet assembly 500 can be used for or with gas-delivery plant-light assembly 102 of FIG. 1C or gas-delivery plant-light assembly 107 of FIG. 1G.

In some embodiments, the low increase in temperature relative to ambient temperature and the direct supply of ducted gas eliminates need for undirected active fans or clunky metal heat sinks, thus lowering the cost of electricity, maintenance and replacement parts. Because of the low temperature rise, the LEDs can be placed right next to the plants (rather than being spaced 18 or more inches away, as is required by high-current LEDs, HPC, metal-halide, fluorescent or other conventional plant lights), thus reducing the volume of space required to grow a given number of plants.

In some embodiments, the low operating temperature relative to other grow-light sources also minimizes fungus and mold resulting from "hot" lighting systems operating indoors, which improves yield and minimizes loss of plants. In some embodiments, one or more UV-B LEDs are included to kill or control fungus such as powdery mildew and the like (in some embodiments, UV-B LEDs on a separately operable circuit such that the UV-B does not expose the crop plants to too much UV-B spectrum light, as well as being able to be turned off when humans are present as a health and safety measure).

In some embodiments, the present invention provides a 12" by 24" 2-mil polyethylene terephthalate (PET)/1-oz. copper flex circuit with 288 LEDs spaced uniformly at one-inch pitch in both the X and Y directions and operating at a power density of 48 W/ft$^2$ can have on the order of 60% (or more) of the substrate removed leaving the circuit containing LEDs intact. Higher power densities can be accommodated by increasing the copper thickness and, if needed, replacing the PET substrate with higher-temperature-capable substrates such as polyethylene naphthalate (PEN) or polyimide.

In some embodiments, larger perforated light sheets (such as 4 feet by 8 feet, which is about 1.22 meters by 2.44 meters) are formed using a plurality of smaller sheets (such as 12" by 24", which is about 30 cm by 60 cm). In some embodiments, various degrees of perforation can be achieved in each 12" by 24" circuit (about 30 cm by about 60 cm circuit; e.g., in some embodiments, containing quantity two-hundred eighty-eight (288) LEDs) as shown in Table 3:

TABLE 3

| Shape | Size | Number of holes | Total open area (in$^2$) | % Open area |
|---|---|---|---|---|
| Circle | 0.25" Dia. | Up to 230 | 11.3 | 3.9 |
| Circle | 0.5" Dia. | Up to 230 | 45.2 | 16 |
| Rectangle | 0.5625" × 0.75" | Up to 230 | 97 | 34 |

In some embodiments, for a circuit of quantity one-hundred forty-four (144) LEDs, there are up to quantity one-hundred ten (110) rectangular openings at 1.75"× 0.5625" and up to quantity ten (10) rectangular openings at 0.75"×0.5625" for a total open area of 112.5 in$^2$, or 39.1%.

In some embodiments, perforated GrowFilm®-brand flexible plant-illumination sheets are used to facilitate air flow, control temperature, and control $CO_2$ and humidity levels. Small perforations can be used with a plenum or perimeter dams (for gases or vapors with a density greater than that of air) to uniformly distribute gases of beneficial composition or water vapor for humidity adjustment.

In some embodiments, the perforated flexible light sheets are formed to have one or more scoop structures associated with each perforation.

It is understood that these inventions can be produced in various shapes and sizes and in a broad range of LED and power densities.

In some embodiments, perforated GrowFilm®-brand flexible plant-illumination sheets are used as tiled sheets, attached to carrier materials (either flexible or rigid), and incorporated into cartridges as described above (e.g., see FIG. 1B1 and FIG. 1B2).

Flexible Plant-Illumination-Sheet Cartridges

In some embodiments, perforated flexible LED plant-illumination sheets (such as GrowFilm®-brand perforated sheets) are incorporated into a plenum cartridge format for use in both vertical and horizontal controlled-environment agriculture (CEA) growing configurations (see FIG. 3). Cartridges can be tiled and ducted together to provide gas delivery across a greater area, either rigidly or hinged, to facilitate use. An example is a 4' by 8' horizontal assembly for use over a horizontal grow bed. Another example is an 8' wide by 28' tall vertical plenum cartridge assembly. Plenum cartridge assemblies can be mounted such that the assembly can be moved across vertical grow walls to provide two zones that can be exposed for equal periods of twelve hours or fractions thereof, or three zones of eight hours each. In similar fashion, plenum cartridge assemblies can be moved to adjacent horizontal beds. In both cases, this reduces the number of cartridges needed to one half to one-third of that which otherwise would be needed.

In some embodiments, power and time are controlled to provide the optimum Daily Light Integral (DLI) and light/dark ratio for the plants being grown. In some embodiments, vertical heights are controlled to allow vertical growth zones. The distance from initial position can be changed to accommodate plant growth for both horizontal bed and vertical wall growth configurations. See also the novel track system of FIG. 3 described above.

In some embodiments, plenum cartridge systems 102A through 102G of FIGS. 1B1 through 1B7, respectively include (in addition to gas ducting connections) modular power and control connections between cartridges and cord management for power and control cords for moveable plenum cartridge assemblies.

In some embodiments, plenum cartridge systems 102B through 102G of FIGS. 1B2 through 1B7, respectively are enclosed with a transparent and cleanable front cover 137 to provide isolation from high voltage for personnel safety, mechanical and environmental protection of the GrowFilm® light sheet, and plenum cartridge wash-down capability.

In some embodiments, used with a front surface transparent cover or without, a GrowFilm® light sheet is optionally protected against water, corrosion, and chemicals with a conformal coating. Parylene, acrylic, polyurethane, and silicone are some of the materials that are used, in some embodiments. In some embodiments, spray, dip, and vacuum deposition are some of the methods for applying the coating. In some embodiments, it is important that the coating used does not adversely affect the performance (color, light output, etc.) of the LEDs. In some embodiments, without a surface in front of the LEDs, the plenum cartridge optionally includes a circumferential and/or intermediate lip on the cartridge. The lip helps protect the LEDs. Further, the lip can be an advantage in a slide-in horizontal rack system so that the rack features do not contact the LEDs.

Novel Track System for Vertical-Grow Gas-Delivery and Light that Accommodates Both Multiple Growth Zones and Adjustable Distance from Plants, to Compensate for Plant Growth.

See FIG. 3. In some embodiments, multiple tracks and switches are provided. In some embodiments, light assemblies 331 (e.g., a plurality of gas-delivery skinny duct light fixtures 340 connected in series) are moved to any of several zones to provide required DLI (Daily Light Integral) and light/dark ratio with fewer light assemblies than would be used with total coverage and turning lighting zones on and off.

In some embodiments, chained and piped/ducted light assemblies 331 (optionally including hinged cartridges) are moved between tracks 321, 322, . . . 329 to maintain optimum plant-to-light distance as plants grow. In some embodiments, light-assembly movement and switching is automated, using electronically controlled motors and switches to move the chained ducted light assemblies 331 to the track location at the desired distance from a first set of plants, and then later move the chained 1 ducted light assemblies 331 to the track location at the desired distance from a second set of plants.

In some embodiments, tracks and switches are at the top of a light assembly or, in other embodiments, at both the top and bottom. If desired, top-only tracks are stabilized at the bottom by, for example, ferromagnetic plates and magnets positioned on the light assemblies and floor as desired. In some embodiments, mechanical positioning features are also or alternatively employed. Please see the discussion regarding FIG. 3.

In some embodiments, the present invention provides a unique flexible printed circuit supporting a two-dimensional (2D) array of LEDs on a perforated sheet that, in some embodiments, is curved to allow growers to light their plants from above, from the side, and from below, resulting in up to a 40% increase in yield. In some embodiments, the flexible printed circuit supporting the 2D array of LEDs forms part of a skinny gas-delivery light fixture that can be used in enclosed high-density grow systems. In some embodiments, the LED light spectrum of the present invention is engineered to provide selected colors and intensities that optimize both yield and quality of all plant varieties— "one light source for all gardens, from tomatoes to *cannabis*." As a result, in some embodiments, the home grower no longer needs three different lighting systems (fluorescent, HPS, and Metal Halide) to accommodate a varietal garden.

In some embodiments, commercial growers can grow high-value crops, such as plants that are bioengineered to form desired pharmaceutical extracts, in a highly controlled high-plant-density indoor environment that is free from pesticides, artificial fertilizers and other contaminates that could degrade the desired pharmaceutical product. Such environments are also useful for other conventional crops such as strawberries and herbs, that consumers want grown organically without chemical pesticides. In some embodiments, the LED sheets include separate sub-circuits for different subpopulations of LEDs so that certain spectral wavelengths can be switched on and off at a schedule that differs from the schedule of other subpopulations of LEDs. For example, in some embodiments, a separately activatable circuit is used for one or more ultraviolet LEDs that emit UV-B wavelengths that are useful for killing or controlling biological pests such as powdery mildew and the like. Such biological pests could otherwise be a problem in very confined high-density grow systems, but where if the UV-B LEDs were left on continuously with the other LEDs, their UV-B light could also be detrimental to the crop plants.

In some other embodiments, the LED light spectrum of the present invention is custom engineered for each one of a plurality of different plant varieties to optimize both yield and quality for each selected plant variety, and to shorten crop turnaround time. For example, different numbers of red LEDs, blue LEDs as well as optional ultraviolet (UV) and/or infrared (IR) are selected based on empirical tests as to how much of each color results in the optimal growth curve. In some such embodiments, a plurality of such sets of LEDs, each set producing light of a different spectrum, are provided, along with circuitry that activates each set or a subset of LEDs in each set based on which variety or type of plant is being grown. In some such embodiments, the circuit is configured to provide different spectra at different plant-growth phases (i.e., certain periods of time such as germination phase, growth phase, flowering phase and the like). In some such embodiments, the circuit is configured to provide light delivered from different directions during different periods of time such that the plant does not need to be rotated due to phototropism (where the plant grows in a particular direction or orientation in response to the direction of light).

In some embodiments, the present invention provides a lighting apparatus that includes a flexible circuit substrate having dimensions of at least 30 cm width and at least 30 cm length, the flexible circuit substrate having a first face and an opposite second face, and a first end and an opposite second end; a first plurality of LEDs affixed to a first face of the flexible circuit substrate, wherein each die of the first plurality of LEDs emits blue light having a peak wavelength in a range of 400 nm and 500 nm, inclusive, and a full-width half-maximum bandwidth of no more than 50 nm; a second plurality of LEDs affixed to the first face of the flexible circuit substrate, wherein each die of the second plurality of LEDs emits red light having a peak wavelength in a range of 600 nm and 700 nm, inclusive, and a full-width half-maximum bandwidth of no more than 50 nm; a third plurality of LEDs affixed to the first face of the flexible circuit substrate, wherein each die of the third plurality of LEDs emits infrared light having a peak wavelength in a range of 700 nm and 800 nm, inclusive, and a full-width half-maximum bandwidth of no more than 50 nm; a first end cap affixed to the first end of the flexible circuit substrate; a second end cap affixed to the second end of the flexible circuit substrate, wherein the first and second end caps are configured to curve the first face of the flexible circuit substrate into a concave shape; and at least a first pole bracket, wherein the first pole bracket is connected to the first end cap, and wherein the first pole bracket is configured to attach to a first pole that supports the lighting apparatus. In some embodiments, ultraviolet LEDs are also included.

In some embodiments, rather than a flexible circuit, a rigid or semi-rigid light-sheet circuit substrate (e.g., in some embodiments, a circuit that is formable by the temporary application of heat to a temperature above the normal operating temperature) is used, wherein the rigid or semi-rigid circuit also provides a thin curved light source that has one or more end caps that provide support and a functionality of attachment to a vertical or horizontal (or other angle) pole.

In some embodiments, the present invention helps feed a hungry planet by optimizing yields for indoor controlled environmental agriculture. In some embodiments, the flexible, low-heat lighting system of the present invention revolutionizes current growing practices. In some conventional systems, yields are limited due to the uneven distribution of vegetative flux. In some embodiments of the present invention, the vegetative flux is redistributed to the plant in a "surround light" distribution that optimizes photosynthesis and resulting yields. In some embodiments, the entire plant (top, middle, and bottom) is fed with a uniform/measured dose of vegetative flux that optimizes yield and quality.

In some embodiments, the present invention is thin and efficient. In some embodiments, the present invention requires no constantly running fan or bulky metal housing to dissipate heat of the LEDs. In some embodiments, the present invention is both minimalistic and functional. In some embodiments, the gas-flow unit (pump, fan or the like) is intermittently activated such that gas is not always flowing towards the crop plants (e.g., in some embodiments, to save energy, a low gas flow or no gas flow is supplied at some times, even at times that the LEDs are fully or partially activated, while at other times a high gas flow is applied (e.g., in some embodiments, in order to provide crop-plant leaf agitation)).

In some conventional plant-growth systems, heat not only stimulates mold and fungus growth, but also consumes non-essential electricity due to additional cooling systems needed, contributing to the high cost of controlled environment agriculture (CEA). In some embodiments, in addition to higher yields, the low-heat delivery system of the present invention contributes to healthier growing environments. In some embodiments, the present invention benefits the grower by significantly increasing yields while reducing unwanted environmental bi-products that reduce plant quality.

In some embodiments, the spectral distribution of the present invention stimulates previously dormant photosynthetic triggers and increases the nutrient values of all plants grown with the present invention. In some embodiments, the present invention includes digital lighting controls to further enhance its benefits. In some embodiments, the present invention includes "tunable" spectrum management and variable intensity control from a remote "smart device" (phone/tablet). In some embodiments, the present invention will allow indoor growers (from hobbyist to professional greenhouse owners) to produce unprecedented yields and profits.

In general, home growers are not optimizing plant yields when using conventional indoor lighting systems because all conventional lighting (including sunlight) produces vegetative light flux delivered exclusively or mostly from an above-the-plant direction, or from only a particular angle from vertical, which produces a "canopy" lighting effect. "Canopy" photosynthesis occurs primarily due to absorption of much of the vegetative light flux at the top (canopy) layer of the plant, resulting in insufficient stimulation of the plant's receptors below the canopy and under the leaf due to the shading and blocking of light by the top layer of vegetation. Consequently, plant growth is less than optimum, and the ensuing long crop-turnaround times negatively impact production and profits of growers.

In some embodiments, the present invention provides a flexible substrate having a plurality of LEDs affixed thereto, such as described in U.S. Pat. No. 8,471,274 to Aaron J. Golle, et al., which is incorporated herein by reference. In some embodiments, the color spectra emitted by a plurality of LEDs are selected to optimize one or more aspects of plant growth. In some embodiments, a large number of LEDs (e.g., in some embodiments, two sets of 144 LEDs per set) are provided, while in other embodiments, some other suitable number of LEDs such as one or more sets, each set having a quantity of 64, 100, 121, 144, 169, 196, 225 or some other suitable number of LEDs, are used), wherein the LEDs are driven with a relatively low amount of electrical current in order to minimize excess heat.

Broad Spectrum of Light

Some embodiments provide a unique vegetative light flux spectral distribution that acts to stimulate plants' photosynthetic triggers to optimize nutrient values and yields.

Flexible Surround Light

Some embodiments provide thin, lightweight, flexible GrowFilm® that can "surround" one or more plants, delivering light and extra yield under the canopy of plants.

All-Inclusive Package

In some embodiments, all elements of the invention that are needed are supplied in one box, with a How-to-Use manual that allows for quick, easy set-up and operation of the lighting system.

In some embodiments, the present invention provides a lighting apparatus that includes a flexible circuit substrate having dimensions of at least 30 cm width and at least 30 cm length, the flexible circuit substrate having a first face and an opposite second face, and a first end and an opposite second end; a first plurality of LEDs affixed to a first face of the flexible circuit substrate, wherein each die of the first plurality of LEDs emits blue light having a peak wavelength in a range of 400 nm and 500 nm, inclusive, and a full-width half-maximum bandwidth of no more than 50 nm; a second plurality of LEDs affixed to the first face of the flexible circuit substrate, wherein each die of the second plurality of LEDs emits red light having a peak wavelength in a range of 600 nm and 700 nm, inclusive, and a full-width half-maximum bandwidth of no more than 50 nm; a third plurality of LEDs affixed to the first face of the flexible circuit substrate, wherein each die of the third plurality of LEDs emits infrared light having a peak wavelength in a range of 700 nm and 800 nm, inclusive, and a full-width half-maximum bandwidth of no more than 50 nm; a first end cap affixed to the first end of the flexible circuit substrate; a second end cap affixed to the second end of the flexible circuit substrate, wherein the first and second end caps are configured to curve the first face of the flexible circuit substrate into a concave shape; and at least a first pole bracket, wherein the first pole bracket is connected to the first end cap, and wherein the first pole bracket is configured to attach to a first pole that supports the lighting apparatus.

In some embodiments of the apparatus, each die of the first plurality of LEDs emits the blue light with a peak wavelength in a range of 420 nm and 480 nm, inclusive, and a full-width half-maximum bandwidth of no more than 20 nm. In some embodiments, each die of the second plurality of LEDs emits the red light with a peak wavelength in a range of 610 nm and 690 nm, inclusive, and a full-width half-maximum bandwidth of no more than 20 nm. In some embodiments, each die of the third plurality of LEDs emits the infrared light with a peak wavelength in a range of 700 nm and 780 nm, inclusive, and a full-width half-maximum bandwidth of no more than 40 nm. In some embodiments, each die of the first plurality of LEDs emits the blue light with a peak wavelength in a range of 420 nm and 480 nm, inclusive, and a full-width half-maximum bandwidth of no more than 20 nm; wherein each die of the second plurality of LEDs emits the red light with a peak wavelength in a range of 610 nm and 690 nm, inclusive, and a full-width half-maximum bandwidth of no more than 20 nm; and wherein each die of the third plurality of LEDs emits the infrared light with a peak wavelength in a range of 700 nm and 780 nm, inclusive, and a full-width half-maximum bandwidth of no more than 40 nm.

In some embodiments, each die of the first plurality of LEDs emits the blue light at a first intensity, wherein each die of the second plurality of LEDs emits the red light at a second intensity, wherein each die of the third plurality of LEDs emits the infrared light at a third intensity, and wherein the first intensity is approximately 50 percent of the second intensity. In some embodiments, each die of the first plurality of LEDs emits the blue light at a first intensity, wherein each die of the second plurality of LEDs emits the red light at a second intensity, wherein each die of the third plurality of LEDs emits the infrared light at a third intensity, wherein the first intensity is approximately 50 percent of the second intensity, and wherein the third intensity is approximately 20 percent of the second intensity. In other embodiments, the third intensity is between about 5 percent and about 15 percent of the second intensity in order to grow crop plants that are shorter and/or more compact than the same type and variety of plants when grown using a spectrum third intensity is approximately 20 percent of the second intensity.

In some embodiments, the apparatus further includes a fourth plurality of LEDs affixed to the first face of the flexible circuit substrate, wherein each die of the fourth plurality of LEDs emits green light having a fourth intensity, a peak wavelength in a range of 500 nm and 560 nm, inclusive, and a full-width half-maximum bandwidth of no more than 60 nm, wherein the fourth intensity is no more than approximately three percent of the second intensity (in other embodiments, the fourth intensity is no more than approximately five percent of the second intensity). In some embodiments, the apparatus further includes a fifth plurality of LEDs affixed to the first face of the flexible circuit substrate, wherein each die of the fifth plurality of LEDs emits white light having a fifth intensity, wherein the fifth intensity is no more than approximately three percent of the second intensity (in other embodiments, the fifth intensity is no more than approximately five percent of the second intensity). In some embodiments, the apparatus further includes a fourth plurality of LED dice affixed to the first face of the flexible circuit substrate, wherein each die of the fourth plurality of LED dice emits green light having a fourth intensity, a peak wavelength in a range of 500 nm and 560 nm, inclusive, and a full-width half-maximum bandwidth of no more than 60 nm, wherein the fourth intensity is no more than approximately three percent of the second intensity (in other embodiments, the fourth intensity is no more than approximately five percent of the second intensity); and a fifth plurality of LED dice affixed to the first face of the flexible circuit substrate, wherein each die of the fifth plurality of LED dice emits white light having a fifth intensity, wherein the fifth intensity is no more than approximately three percent of the second intensity (in other embodiments, the fifth intensity is no more than approximately five percent of the second intensity). In some embodiments, the apparatus further includes a fourth plurality of LED dice affixed to the first face of the flexible circuit substrate, wherein each die of the fourth plurality of LED dice emits green light having a fourth intensity, a peak wavelength in a range of 500 nm and 560 nm, inclusive, and a full-width half-maximum bandwidth of no more than 60 nm, wherein the fourth intensity is no more than approximately three percent of the second intensity (in other embodiments, the fourth intensity is no more than approximately five percent of the second intensity); and a sixth plurality of LED dice affixed to the first face of the flexible circuit substrate, wherein each die of the fifth plurality of LED dice emits yellow light having a sixth intensity, wherein the sixth intensity is no more than approximately three percent of the second intensity (in other embodiments, the sixth intensity is no more than approximately five percent of the second intensity).

In some embodiments, the present invention provides a method that includes providing a flexible circuit substrate having dimensions of at least 30 cm width and at least 30 cm length, the flexible circuit substrate having a first face on a first side and an opposite second face on an opposite second side, and a first end and an opposite second end; affixing a first plurality of LED dice to a first face of the flexible circuit substrate; emitting from each die of the first plurality of LED dice blue light having a peak wavelength in a range of 400 nm and 500 nm, inclusive, and a full-width half-maximum bandwidth of no more than 50 nm; affixing a second plurality of LED dice to the first face of the flexible circuit substrate; emitting from each die of the second plurality of LED dice red light having a peak wavelength in a range of 600 nm and 700 nm, inclusive, and a full-width half-maximum bandwidth of no more than 50 nm; affixing a third plurality of LED dice affixed to the first face of the flexible circuit substrate; emitting from each die of the third plurality of LED dice infrared light having a peak wavelength in a range of 700 nm and 800 nm, inclusive, and a full-width half-maximum bandwidth of no more than 50 nm; attaching a first end cap to the first end of the flexible circuit substrate; attaching a second end cap to the second end of the flexible circuit substrate, wherein the attaching of the first and second end caps includes curving the first face of the flexible circuit substrate into a concave shape; and supporting the lighting apparatus, wherein the supporting includes connecting a first pole to the first end cap.

In some embodiments, the method further includes mounting the flexible circuit substrate in a vertical orientation. In some embodiments, the method further includes mounting the flexible circuit substrate in a horizontal orientation. In some embodiments, the flexible circuit substrate is a first flexible circuit substrate of a plurality of flexible circuit substrates, the method further includes mounting each one of the plurality of flexible circuit substrates in a desired orientation.

In some embodiments of the method, the emitting from each die of the first plurality of LED dice includes emitting the blue light with a peak wavelength in a range of 420 nm and 480 nm, inclusive, and a full-width half-maximum bandwidth of no more than 20 nm. In some embodiments, the emitting from each die of the second plurality of LED dice includes emitting the red light with a peak wavelength in a range of 610 nm and 690 nm, inclusive, and a full-width half-maximum bandwidth of no more than 20 nm. In some embodiments, the emitting from each die of the third plurality of LED dice includes emitting the infrared light with a peak wavelength in a range of 700 nm and 780 nm, inclusive, and a full-width half-maximum bandwidth of no more than 40 nm. In some embodiments, the emitting from each die of the first plurality of LED dice includes emitting the blue light with a peak wavelength in a range of 420 nm and 480 nm, inclusive, and a full-width half-maximum bandwidth of no more than 20 nm; wherein the emitting from each die of the second plurality of LED dice includes emitting the red light with a peak wavelength in a range of 610 nm and 690 nm, inclusive, and a full-width half-maximum bandwidth of no more than 20 nm; and wherein the emitting from each die of the third plurality of LED dice includes emitting the infrared light with a peak wavelength in a range of 700 nm and 780 nm, inclusive, and a full-width half-maximum bandwidth of no more than 40 nm.

In some embodiments, the present invention provides a method that includes providing a flexible circuit substrate having dimensions of at least 30 cm width and at least 30 cm length, the flexible circuit substrate having a first face on a first side and an opposite second face on an opposite second side, and a first end and an opposite second end; affixing a first plurality of LED dice to a first face of the flexible circuit substrate; emitting from each die of the first plurality of LED dice blue light having a peak wavelength in a range of 400 nm and 500 nm, inclusive, and a full-width half-maximum bandwidth of no more than 50 nm; affixing a second plurality of LED dice to the first face of the flexible circuit substrate; emitting from each die of the second plurality of LED dice red light having a peak wavelength in a range of 600 nm and 700 nm, inclusive, and a full-width half-maximum bandwidth of no more than 50 nm; affixing a third plurality of LED dice affixed to the first face of the flexible circuit substrate; emitting from each die of the third plurality of LED dice infrared light having a peak wavelength in a range of 700 nm and 800 nm, inclusive, and a full-width half-maximum bandwidth of no more than 50 nm. In some embodiments of this method, the emitting from each die of the first plurality of LED dice includes emitting the blue light with a peak wavelength in a range of 440 nm and 460 nm, inclusive, and a full-width half-maximum bandwidth of no more than 30 nm; wherein the emitting from each die of the second plurality of LED dice includes emitting the cyan light with a peak wavelength in a range of 490 nm and 510 nm, inclusive, and a full-width half-maximum bandwidth of no more than 30 nm; wherein the emitting from each die of the third plurality of LED dice includes emitting the red light with a peak wavelength in a range of 610 nm and 650 nm, inclusive, and a full-width half-maximum bandwidth of no more than 30 nm; wherein the emitting from each die of the fourth plurality of LED dice includes emitting the infrared light with a peak wavelength in a range of 700 nm and 780 nm, inclusive, and a full-width half-maximum bandwidth of no more than 40 nm. In some embodiments, the emitting from each die of a fifth plurality of LED dice includes emitting the ultraviolet light with a peak wavelength in a range of 370 nm and 390 nm, inclusive, and a full-width half-maximum bandwidth of no more than 20 nm. In some embodiments, the emitting from each die of a sixth plurality of LED dice includes emitting the violet light with a peak wavelength in a range of 410 nm and 420 nm, inclusive, and a full-width half-maximum bandwidth of no more than 30 nm. In some embodiments, the method further includes using one or more LED dice that emit green light with a peak wavelength in a range of 530 nm and 570 nm, inclusive, and a full-width half-maximum bandwidth of no more than 30 nm. In some embodiments, the method further includes using one or more LED dice that emit yellow light with a peak wavelength in a range of 570 nm and 590 nm, inclusive, and a full-width half-maximum bandwidth of no more than 30 nm.

In some embodiments of the method, the emitting from each die of the first plurality of LED dice includes emitting the blue light at a first intensity, wherein the emitting from each die of the second plurality of LED dice includes emitting the red light at a second intensity, wherein the emitting from each die of the third plurality of LED dice includes emitting the infrared light at a third intensity, and wherein the first intensity is approximately 50 percent of the second intensity. In some embodiments, the emitting from each die of the first plurality of LED dice includes emitting the blue light at a first intensity, wherein the emitting from each die of the second plurality of LED dice includes emitting the red light at a second intensity, wherein the emitting from each die of the third plurality of LED dice includes emitting the infrared light at a third intensity, wherein the first intensity is approximately 50 percent of the second intensity, and wherein the third intensity is approximately 20 percent of the second intensity.

In some embodiments, the method further includes affixing a fourth plurality of LED dice to the first face of the flexible circuit substrate; and emitting from each die of the fourth plurality of LED dice green light having a fourth intensity, a peak wavelength in a range of 500 nm and 560 nm, inclusive, and a full-width half-maximum bandwidth of no more than 60 nm, wherein the fourth intensity is no more than approximately three (3) percent of the second intensity. In some embodiments, the method further includes affixing a fifth plurality of LED dice affixed to the first face of the flexible circuit substrate; and emitting from each die of the fifth plurality of LED dice white light having a fifth intensity, wherein the fifth intensity is no more than approximately three (3) percent of the second intensity. In some embodiments, the method further includes affixing a fourth plurality of LED dice to the first face of the flexible circuit substrate; emitting from each die of the fourth plurality of LED dice green light having a fourth intensity, a peak wavelength in a range of 500 nm and 560 nm, inclusive, and a full-width half-maximum bandwidth of no more than 60 nm, wherein the fourth intensity is no more than approximately three (3) percent of the second intensity; affixing a fifth plurality of LED dice affixed to the first face of the flexible circuit substrate; and emitting from each die of the fifth plurality of LED dice white light having a fifth intensity, wherein the fifth intensity is no more than approximately three (3) percent of the second intensity.

In some embodiments, the present invention provides an apparatus for mass production of plants, the apparatus including: a plant-light system that includes a plurality of plant-lighting sheets, wherein each plant-lighting sheet includes a plurality of LED tiles, each LED tile including a plurality of LEDs arranged on a grid, the plurality of LEDs including LEDs emitting light that appears red, light that appears blue and light that appears white, wherein each plant lighting sheet has a length and a width, wherein the length of each plant lighting sheet is at least five times the width, and wherein the plurality of lighting sheets is arranged along a length of a room; a plant-sheet rotation and withdrawal system arranged to rotate one or more of the plant lighting sheets between a first orientation substantially parallel relative to the length of the room and a second orientation substantially perpendicular relative to the length of the room; and a plurality of plant-holding shelves arranged along the length of the room facing the plurality of plant lighting sheets.

In some embodiments, the present invention provides an apparatus for mass production of plants, the apparatus including: a plant-light system that includes a plurality of plant-lighting sheets, wherein each plant-lighting sheet includes one or more LED tiles, each LED tile including a plurality of LEDs arranged on a grid; a plurality of parallel tracks for arranging the plurality of plant-lighting sheets; a plant-sheet movement system arranged to move one or more of the plant lighting sheets between a first location substantially parallel relative to the length of the room and a second location substantially parallel relative to the length of the room; and a plurality of plant-holding shelves arranged along the length of the room facing the plurality of plant lighting sheets, wherein the plurality of parallel tracks allows the plurality of plant-lighting sheets to be located at a plurality of different distances from the plant-holding shelves.

In some embodiments, the present invention provides an apparatus that includes: a first perforated plant-lighting sheet having a plurality of LEDs mounted thereon in a grid wired in parallel-series connected by a plurality of series conductors and a plurality of parallel conductors, wherein the first plant-lighting sheet has a plurality of holes therethrough, each of the plurality of holes located between two adjacent ones of the plurality of series conductors and between two adjacent ones of the plurality of parallel conductors.

Some embodiments further include a second perforated plant-lighting sheet having a plurality of LEDs mounted thereon in a grid wired in parallel-series connected by a plurality of series conductors and a plurality of parallel conductors, wherein the second plant-lighting sheet has a plurality of holes therethrough, each of the plurality of holes located between two adjacent ones of the plurality of series conductors and between two adjacent ones of the plurality of parallel conductors, and wherein the first plant-lighting sheet and the second plant-lighting sheet are stacked one on the other such that light from the LEDs on the second plant-lighting sheet is emitted through the holes of the first plant-lighting sheet.

In some embodiments, the present invention provides an apparatus that includes: a plant-lighting plenum cartridge that includes: a first front-side plant-lighting sheet system having a plurality of LEDs mounted thereon in a grid wired in parallel-series connected by a plurality of series conductors and a plurality of parallel conductors; a raised lip surrounding the first plant-lighting sheet such that the LEDs are recessed from the outer edge of the raised lip; and a backside electronics enclosure that contains power-supply electronics that are operatively coupled to the plurality of LEDs.

In some embodiments, the plant-lighting sheet system further includes a plurality of perforated plant-lighting sheets including a first perforated plant-lighting sheet having a plurality of LEDs mounted thereon in a grid wired in parallel-series connected by a plurality of series conductors and a plurality of parallel conductors, wherein the first plant-lighting sheet has a plurality of holes therethrough, each of the plurality of holes located between two adjacent ones of the plurality of series conductors and between two adjacent ones of the plurality of parallel conductors, and a second perforated plant-lighting sheet having a plurality of LEDs mounted thereon in a grid wired in parallel-series connected by a plurality of series conductors and a plurality of parallel conductors, wherein the second plant-lighting sheet has a plurality of holes therethrough, each of the plurality of holes located between two adjacent ones of the plurality of series conductors and between two adjacent ones of the plurality of parallel conductors, and wherein the first plant-lighting sheet and the second plant-lighting sheet are stacked one on the other such that light from the LEDs on the second plant-lighting sheet is emitted through the holes of the first plant-lighting sheet.

In some embodiments, the present invention provides a gas-delivery lighting apparatus that includes a housing; a first circuit substrate having a plurality of perforations, the substrate connected to the housing, wherein the circuit substrate has a plurality of conductors on a first face of the first circuit substrate; a first plurality of LEDs affixed to the plurality of conductors, wherein the plurality of conductors form a parallel-series circuit with the LEDs; and a first gas conduit operably coupled to the housing, wherein the housing is configured so that gas delivered to the housing through the first gas conduit is emitted through the plurality of perforations.

Some embodiments further include a perforated transparent sheet disposed over the LEDs and operatively coupled to the circuit substrate with a plurality of connectors that pass the gas through openings in the plurality of connectors.

In some embodiments, the circuit substrate is a flexible circuit substrate.

In some embodiments, each one of the first plurality of LEDs emits the red light with a peak wavelength in a range of 610 nm and 690 nm, inclusive, and a full-width half-maximum bandwidth of no more than 20 nm, and wherein the gas-delivery lighting apparatus further includes: a second plurality of LEDs affixed to the conductors, wherein each one of the second plurality of LEDs emits the infrared light with a peak wavelength in a range of 700 nm and 780 nm, inclusive, and a full-width half-maximum bandwidth of no more than 40 nm; and a third plurality of LEDs affixed to the conductors, wherein each one of the third plurality of LEDs emits the blue light with a peak wavelength in a range of 420 nm and 480 nm, inclusive, and a full-width half-maximum bandwidth of no more than 20 nm.

In some embodiments, each die of the first plurality of LED dice emits the blue light at a first intensity, wherein each die of the second plurality of LED dice emits the red light at a second intensity, wherein each die of the third plurality of LED dice emits the infrared light at a third intensity, and wherein the first intensity is approximately 50 percent of the second intensity.

In some embodiments, the first gas conduit includes a fan housing with an electrically powered fan mounted therein.

In some embodiments, the first gas conduit is attached to an electrically powered fan.

In some embodiments, the first gas conduit is attached to an air pump that forces gas through the gas-delivery lighting apparatus.

In some embodiments, the first gas conduit includes an audio transducer that, at least periodically, applies an audio signal of about 600 hertz into the first gas conduit. In some embodiments, the audio signal assists crop-plant pollination.

Some embodiments further include a source of one or more aromatic chemicals useful for aroma therapy; a temperature-adjustment device operatively coupled to the first gas conduit; and a controller operatively coupled to the source of one or more aromatic chemicals, to the temperature-adjustment device, and to the conductors coupled to the first plurality of LEDs and configured to allow user control of the light, aroma therapy and gas temperature.

In some embodiments, the circuit substrate includes a plurality of layers of circuitry each on a separate one of a plurality of perforated circuitry sheets, wherein each one of the plurality of perforated circuitry sheets includes a plurality of LEDs.

Some embodiments further include a source of one or more photosensitizing chemicals useful for therapy; and a controller operatively coupled to the source of one or more photosensitizing chemicals configured to allow a health professional to control of the light, and photosensitizing chemical delivery.

Some embodiments further include a source of one or more plant fertilizer chemicals useful for plant growth; and a controller operatively coupled to the source of one or more photosensitizing chemicals configured to allow a worker to control of the light, and plant fertilizer chemical delivery.

In some embodiments, the present invention provides a method that includes providing a housing connected to a perforated circuit substrate having a plurality of electrical conductors on a first face of the circuit substrate and a plurality of perforations through the substrate and a first plurality of LEDs affixed to the plurality of electrical conductors; delivering a gas to the housing such that the gas is emitted out through the plurality of perforations; and delivering electrical power to the first plurality of LEDs such that light is emitted from each of the first plurality of LEDs.

In some embodiments, the delivering of the gas to the housing includes using a fan to blow air into the housing.

In some embodiments, the delivering of the gas to the housing includes delivering carbon dioxide from a compressed source of carbon dioxide.

In some embodiments, each one of the first plurality of LEDs emits the red light with a peak wavelength in a range of 610 nm and 690 nm, inclusive, and a full-width half-maximum bandwidth of no more than 20 nm, and wherein the gas-delivery lighting apparatus further includes: a second plurality of LEDs affixed to the conductors, wherein each one of the second plurality of LEDs emits the infrared light with a peak wavelength in a range of 700 nm and 780 nm, inclusive, and a full-width half-maximum bandwidth of no more than 40 nm; and a third plurality of LEDs affixed to the conductors, wherein each one of the third plurality of LEDs emits the blue light with a peak wavelength in a range of 420 nm and 480 nm, inclusive, and a full-width half-maximum bandwidth of no more than 20 nm. In some such embodiments, each die of the first plurality of LED dice emits the blue light at a first intensity, wherein each die of the second plurality of LED dice emits the red light at a second intensity, wherein each die of the third plurality of LED dice emits the infrared light at a third intensity, and wherein the first intensity is approximately 50 percent of the second intensity.

In some embodiments, the gas is pushed with an electrically powered fan mounted therein.

Some embodiments further include a source of one or more aromatic chemicals useful for aroma therapy; temperature-adjusting gas; and controlling the one or more aromatic chemicals, the temperature-adjustment device, and the conductors coupled to the first plurality of LEDs and configured to allow user control of the light, aroma therapy and gas temperature.

Some embodiments include a lighting apparatus that includes a flexible circuit substrate that has a front face and an opposite back face, and a first end and an opposite second end; a first plurality of LEDs on the flexible substrate, wherein each die of the first plurality of LEDs emits blue light; a second plurality of LEDs that emits red light; a third plurality of LEDs that emits infrared, wherein the first, second and third plurality of LEDs each emit a full-width-half-maximum bandwidth of no more than 50 nm in each of their respective colors. Some embodiments provide variable spacing to the apparatus and variable scheduled lighting periods and accommodate various types of botanical plants.

In some embodiments, the present invention provides a gas-delivery lighting apparatus for mass production of plants, wherein the apparatus includes a plant-light system that includes a plurality of ducted plant-lighting plenum sheets, wherein each ducted plant-lighting plenum sheet includes a plurality of perforated LED tiles, each LED tile including a plurality of LEDs arranged on a grid, the plurality of LEDs including LEDs emitting light that appears red, light that appears blue, light that appears white, and light that is at least mostly infrared light, wherein each plant lighting sheet has a length and a width, and wherein the plurality of lighting sheets is arranged along a length of a room; a plurality of plant-holding pockets arranged along the length of the room generally parallel to the plurality of ducted plant-lighting plenum sheets; and a plant-lighting plenum sheets motion and withdrawal system arranged to move the plurality of ducted plant-lighting plenum sheets to a plurality of different locations relative to the plurality of plant-holding pockets for different time periods. Some embodiments further include a plurality of shelves, wherein the plurality of plant-holding pockets includes a plurality of pots configured to hold soil or soil substitute for growing plants, and wherein the pots of the plurality of pots are supported by the plurality of shelves (for example, see FIG. 3). Some other embodiments further include a support sheet supported vertically, wherein the plurality of plant-holding pockets are attached to or formed from the support sheet and each of the plurality of plant-holding pockets is configured to hold one or more crop plants during a growth period of the crop plants (for example, see FIG. 1H1, FIG. 1H2, FIG. 1H3, and/or FIG. 1H4).

In some embodiments, the present invention provides a gas-delivery lighting apparatus that includes a plant-light system that includes a plurality of ducted plant-lighting plenum sheets, wherein each ducted plant-lighting plenum sheet includes a plurality of LED tiles, each LED tile including a plurality of LEDs arranged on a grid, the plurality of LEDs including LEDs emitting light that appears red, light that appears blue and light that appears white, wherein each plant lighting sheet has a length and a width, wherein the length of each plant lighting sheet is at least five times the width, and wherein the plurality of lighting sheets is arranged along a length of a room; a plant-sheet rotation and withdrawal system arranged to rotate one or more of the plant lighting sheets between a first orientation substantially parallel relative to the length of the room and a second orientation substantially perpendicular relative to the length of the room; and a plurality of plant-holding shelves arranged along the length of the room facing the plurality of plant lighting sheets.

In some embodiments, the present invention provides a gas-delivery lighting apparatus that includes a plant-light system that includes a plurality of ducted plant-lighting plenum sheets, wherein each ducted plant-lighting plenum sheet includes one or more LED tiles, each LED tile including a plurality of LEDs arranged on a grid; a plurality of parallel tracks for arranging the plurality of ducted plant-lighting plenum sheets; a plant-sheet movement system arranged to move one or more of the plant lighting sheets between a first location substantially parallel relative to the length of the room and a second location substantially parallel relative to the length of the room; and a plurality of plant-holding shelves arranged along the length of the room facing the plurality of plant lighting sheets, wherein the plurality of parallel tracks allows the plurality of ducted plant-lighting plenum sheets to be located at a plurality of different distances from the plant-holding shelves.

In some embodiments, the present invention provides a gas-delivery lighting apparatus that includes a first perforated ducted plant-lighting plenum sheet having a plurality of LEDs mounted thereon in a grid wired in parallel-series connected by a plurality of series conductors and a plurality of parallel conductors, wherein the first ducted plant-lighting plenum sheet has a plurality of holes therethrough, each of the plurality of holes located between two adjacent ones of the plurality of series conductors and between two adjacent ones of the plurality of parallel conductors. Some embodiments further include a second perforated ducted plant-lighting plenum sheet having a plurality of LEDs mounted thereon in a grid wired in parallel-series connected by a plurality of series conductors and a plurality of parallel conductors, wherein the second ducted plant-lighting plenum sheet has a plurality of holes therethrough, each of the plurality of holes located between two adjacent ones of the plurality of series conductors and between two adjacent ones of the plurality of parallel conductors, and wherein the first ducted plant-lighting plenum sheet and the second ducted plant-lighting plenum sheet are stacked one on the other such that light from the LEDs on the second ducted plant-lighting plenum sheet is emitted through the holes of the first ducted plant-lighting plenum sheet.

In some embodiments, the present invention provides a gas-delivery lighting apparatus that includes a ducted plant-lighting plenum cartridge that includes: a first front-side ducted plant-lighting plenum sheet system having a plurality of LEDs mounted thereon in a grid wired in parallel-series connected by a plurality of series conductors and a plurality of parallel conductors; a raised lip surrounding the first ducted plant-lighting plenum sheet such that the LEDs are recessed from the outer edge of the raised lip; and a backside electronics enclosure that contains power-supply electronics that are operatively coupled to the plurality of LEDs. In some such embodiments, the ducted plant-lighting plenum sheet system further includes a plurality of perforated ducted plant-lighting plenum sheets including a first perforated ducted plant-lighting plenum sheet having a plurality of LEDs mounted thereon in a grid wired in parallel-series connected by a plurality of series conductors and a plurality of parallel conductors, wherein the first ducted plant-lighting plenum sheet has a plurality of holes therethrough, each of the plurality of holes located between two adjacent ones of the plurality of series conductors and between two adjacent ones of the plurality of parallel conductors, and a second perforated ducted plant-lighting plenum sheet having a plurality of LEDs mounted thereon in a grid wired in parallel-series connected by a plurality of series conductors and a plurality of parallel conductors, wherein the second ducted plant-lighting plenum sheet has a plurality of holes therethrough, each of the plurality of holes located between two adjacent ones of the plurality of series conductors and between two adjacent ones of the plurality of parallel conductors, and wherein the first ducted plant-lighting plenum sheet and the second ducted plant-lighting plenum sheet are stacked one on the other such that light from the LEDs on the second ducted plant-lighting plenum sheet is emitted through the holes of the first ducted plant-lighting plenum sheet.

In some embodiments, the present invention provides a gas-delivery lighting apparatus that includes a plant-light system that includes a plurality of rows of ducted plant-lighting plenum sheets, wherein each one of the plurality of rows of ducted plant-lighting plenum sheets includes plurality of ducted plant-lighting plenum sheets, wherein each one of the plurality of ducted plant-lighting plenum sheets of each of the plurality of rows of ducted plant-lighting plenum sheets includes one or more LED tiles, each LED tile including a plurality of LEDs arranged on a grid, and wherein each of the plurality of ducted plant-lighting plenum sheets of each of the plurality of rows of ducted plant-lighting plenum sheets is rotatable around a vertical axis; a plant-sheet rotation system arranged to rotate the plurality of ducted plant-lighting plenum sheets of each of the plurality of rows of ducted plant-lighting plenum sheets between a first orientation substantially facing a first direction relative to a length of the lighting row and a second direction substantially opposite the first direction; and a plurality of plant-holding shelves arranged between each pair of rows of the plurality of rows of ducted plant-lighting plenum sheets along the lengths of the rows, wherein the plant-sheet rotation system is configured to rotate each pair of rows of the plurality of rows of ducted plant-lighting plenum sheets to face towards a different one of the plurality of plant-holding shelves for a first period of time, and then to rotate each the plurality of rows of ducted plant-lighting plenum sheets to face a different one of the plurality of plant-holding shelves for a second period of time that alternates with the first period. In some embodiments, for a first period of twelve hours each day, all of the light sheets are in alternating directions of a first configuration and face the even-numbered ones of the plurality of plant-holding shelves, and at the end of that first period, all of the light sheets of each row are rotated around their respective vertical axes to face the opposite direction for a next 12-hour period. In some embodiments, for a first period of eight hours each day, all of the light sheets are in alternating directions of a first configuration and face the even-numbered ones of the plurality of plant-holding shelves, and at the end of that first period, all of the light sheets of each row are rotated around their respective vertical axes to face the opposite direction for a next eight-hour period. In some embodiments, for a first period of time, all of the light sheets are in alternating directions of a first configuration and face the even-numbered ones of the plurality of plant-holding shelves, and at the end of that first period, all of the light sheets of each row are rotated around their respective vertical axes to face the opposite direction for a next period of time.

It is to be understood that the above description is intended to be illustrative, and not restrictive. Although numerous characteristics and advantages of various embodiments as described herein have been set forth in the foregoing description, together with details of the structure and function of various embodiments, many other embodiments and changes to details will be apparent to those of skill in the art upon reviewing the above description. The scope of the invention should be, therefore, determined with reference to the appended claims, along with the full scope of equivalents to which such claims are entitled. In the appended claims, the terms "including" and "in which" are used as the plain-English equivalents of the respective terms "comprising" and "wherein," respectively. Moreover, the terms "first, " "second," and "third," etc., are used merely as labels, and are not intended to impose numerical requirements on their objects.

What is claimed is:

1. A gas-delivery lighting apparatus comprising:
   a housing having a support structure;
   a first circuit substrate having a first plurality of perforations, the first circuit substrate connected to the support structure on a first side of the support structure, wherein the first circuit substrate has a first plurality of conductors on a first face of the first circuit substrate;
   a first plurality of LEDs affixed to the first plurality of conductors, wherein the first plurality of conductors form a parallel-series circuit with the first plurality of LEDs;
   a second circuit substrate having a second plurality of perforations, the second circuit substrate connected to the support structure on a second side of the support structure, opposite the first side, wherein the second circuit substrate has a second plurality of conductors on a first face of the second circuit substrate;
   a second plurality of LEDs affixed to the second plurality of conductors, wherein the second plurality of conductors form a parallel-series circuit with the second plurality of LEDs; and
   a first gas conduit operably coupled to the housing, wherein the housing is configured so that gas delivered to the housing through the first gas conduit is emitted through the first plurality of perforations and through the second plurality of perforations.

2. The gas-delivery lighting apparatus of claim 1, further comprising a first perforated transparent sheet disposed over the LEDs of the first circuit substrate and operatively coupled to the first circuit substrate with a plurality of connectors that pass the gas through openings in the plurality of connectors.

3. The gas-delivery lighting apparatus of claim 2, further comprising a second perforated transparent sheet disposed over the LEDs of the second circuit substrate and operatively coupled to the second circuit substrate with a plurality of connectors that pass the gas through openings in the plurality of connectors, and wherein the first perforated transparent sheet and the second perforated transparent sheet form outer walls for the housing.

4. The gas-delivery lighting apparatus of claim 1, wherein the circuit substrate is a flexible circuit substrate.

5. The gas-delivery lighting apparatus of claim 1, wherein each one of the first plurality of LEDs emits red light with a peak wavelength in a range of 610 nm to 690 nm, inclusive, and a full-width half-maximum bandwidth of no more than 20 nm, and wherein the gas-delivery lighting apparatus further includes:
   a second plurality of LEDs affixed to the conductors, wherein each one of the second plurality of LEDs emits infrared light with a peak wavelength in a range of 700 nm to 780 nm, inclusive, and a full-width half-maximum bandwidth of no more than 40 nm; and
   a third plurality of LEDs affixed to the conductors, wherein each one of the third plurality of LEDs emits blue light with a peak wavelength in a range of 420 nm to 480 nm, inclusive, and a full-width half-maximum bandwidth of no more than 20 nm.

6. The gas-delivery lighting apparatus of claim 1, further comprising:
   a source of one or more aromatic chemicals useful for aroma therapy;
   a temperature-adjustment device operatively coupled to the first gas conduit; and
   a controller operatively coupled to the source of one or more aromatic chemicals, to the temperature-adjustment device, and to the first plurality of conductors coupled to the first plurality of LEDs, the controller configured to allow user control of light, the aroma therapy and gas temperature.

7. The gas-delivery lighting apparatus of claim 1, wherein the first circuit substrate includes a plurality of layers of circuitry each on a separate one of a plurality of perforated circuitry sheets, wherein each one of the plurality of perforated circuitry sheets includes a plurality of LEDs.

8. The gas-delivery lighting apparatus of claim 1, further comprising:
   a source of one or more photosensitizing chemicals useful for therapy; and
   a controller operatively coupled to the source of one or more photosensitizing chemicals, the controller configured to allow a health professional to control light and photosensitizing chemical delivery.

9. The gas-delivery lighting apparatus of claim 1, further comprising:
   a source of one or more plant fertilizer chemicals useful for plant growth; and
   a controller operatively coupled to the source of one or more plant fertilizer chemicals, the controller configured to allow a worker to control light and plant fertilizer chemical delivery.

10. The gas-delivery lighting apparatus of claim 1, wherein each one of the first plurality of LEDs emits red light with a peak wavelength in a range of 610 nm to 690 nm, inclusive, and a full-width half-maximum bandwidth of no more than 20 nm, and wherein the gas-delivery lighting apparatus further comprises:
   a second plurality of LEDs affixed to the conductors, wherein each one of the second plurality of LEDs emits infrared light with a peak wavelength in a range of 700 nm to 780 nm, inclusive, and a full-width half-maximum bandwidth of no more than 40 nm;

a third plurality of LEDs affixed to the conductors, wherein each one of the third plurality of LEDs emits blue light with a peak wavelength in a range of 420 nm to 480 nm, inclusive, and a full-width half-maximum bandwidth of no more than 20 nm; and a perforated transparent sheet disposed over the first, second, and third plurality of LEDs and operatively coupled to the first circuit substrate with a plurality of connectors that pass the gas through openings in the plurality of connectors.

11. The gas-delivery lighting apparatus of claim 1, wherein the first circuit substrate is a flexible circuit substrate, wherein each one of the first plurality of LEDs emits red light with a peak wavelength in a range of 610 nm to 690 nm, inclusive, and a full-width half-maximum bandwidth of no more than 20 nm, and wherein the gas-delivery lighting apparatus further includes:

a second plurality of LEDs affixed to the conductors, wherein each one of the second plurality of LEDs emits infrared light with a peak wavelength in a range of 700 nm to 780 nm, inclusive, and a full-width half-maximum bandwidth of no more than 40 nm; and a third plurality of LEDs affixed to the conductors, wherein each one of the third plurality of LEDs emits blue light with a peak wavelength in a range of 420 nm to 480 nm, inclusive, and a full-width half-maximum bandwidth of no more than 20 nm.

12. The gas-delivery lighting apparatus of claim 1, further comprising a perforated transparent sheet disposed over the first plurality of LEDs and operatively coupled to the first circuit substrate with a plurality of connectors that pass the gas through openings in the plurality of connectors, wherein the first gas conduit includes:

a fan housing with an electrically powered fan mounted therein; and an audio transducer that, at least periodically, applies an audio signal of about 600 hertz into the first gas conduit.

13. The gas-delivery lighting apparatus of claim 1, wherein the first circuit substrate is a flexible circuit substrate, wherein the first gas conduit includes:

a fan housing with an electrically powered fan mounted therein; and an audio transducer that, at least periodically, applies an audio signal of about 600 hertz into the first gas conduit.

14. The gas-delivery lighting apparatus of claim 1, wherein the first circuit substrate is a flexible circuit substrate, and wherein the first circuit substrate includes a plurality of layers of circuitry each on a separate one of a plurality of perforated circuitry sheets, and wherein each one of the plurality of perforated circuitry sheets includes a plurality of LEDs.

15. The gas-delivery lighting apparatus of claim 1, wherein the first circuit substrate is a flexible circuit substrate, wherein the first circuit substrate includes a plurality of layers of circuitry each on a separate one of a plurality of perforated circuitry sheets, wherein each one of the plurality of perforated circuitry sheets includes a plurality of LEDs, and wherein the first gas conduit includes:

a fan housing with an electrically powered fan mounted therein; and an audio transducer that, at least periodically, applies an audio signal of about 600 hertz into the first gas conduit.

16. The gas-delivery lighting apparatus of claim 1, wherein the first circuit substrate and the second circuit substrate form outer walls for the housing.

17. A gas-delivery lighting apparatus comprising:

a housing;

a first circuit substrate having a plurality of perforations, the substrate connected to the housing, wherein the circuit substrate has a plurality of conductors on a first face of the first circuit substrate;

a first plurality of LEDs affixed to the plurality of conductors, wherein the plurality of conductors form a parallel-series circuit with the LEDs, wherein each one of the first plurality of LEDs emits red light with a peak wavelength in a range of 610 nm to 690 nm, inclusive, and a full-width half-maximum bandwidth of no more than 20 nm;

a first gas conduit operably coupled to the housing, wherein the housing is configured so that gas delivered to the housing through the first gas conduit is emitted through the plurality of perforations;

a second plurality of LEDs affixed to the conductors, wherein each one of the second plurality of LEDs emits infrared light with a peak wavelength in a range of 700 nm to 780 nm, inclusive, and a full-width half-maximum bandwidth of no more than 40 nm; and a third plurality of LEDs affixed to the conductors, wherein each one of the third plurality of LEDs emits blue light with a peak wavelength in a range of 420 nm to 480 nm, inclusive, and a full-width half-maximum bandwidth of no more than 20 nm, wherein each die of the first plurality of LED dice emits the blue light at a first intensity, wherein each die of the second plurality of LED dice emits the red light at a second intensity, wherein each die of the third plurality of LED dice emits the infrared light at a third intensity, and wherein the first intensity is 50 percent of the second intensity.

18. The gas-delivery lighting apparatus of claim 17, wherein the first gas conduit includes:

a fan housing with an electrically powered fan mounted therein; and an audio transducer that, at least periodically, applies an audio signal of about 600 hertz into the first gas conduit.

19. An apparatus for mass production of plants, the apparatus comprising:

a plant-light system that includes a plurality of ducted plant-lighting plenum sheets, wherein each one of the plurality of ducted plant-lighting plenum sheets includes:

a housing having a support structure, a first circuit substrate having a first plurality of perforations, the first circuit substrate connected to the support structure on a first side of the support structure, wherein the first circuit substrate has a first plurality of conductors on a first face of the first circuit substrate, a first plurality of LEDs affixed to the first plurality of conductors, wherein the first plurality of conductors form a parallel-series circuit with the first plurality of LEDs, a second circuit substrate having a second plurality of perforations, the second circuit substrate connected to the support structure on a second side of the support structure, opposite the first side, wherein the second circuit substrate has a second plurality of conductors on a first face of the second circuit substrate, a second plurality of LEDs affixed to the second plurality of conductors, wherein the second plurality of conductors form a parallel-series circuit with the second plurality of LEDs, and a first gas conduit operably coupled to the housing, wherein the housing is configured so that gas delivered to the housing through the first gas conduit is emitted through the first plurality of perforations and through the second plurality of perforations, wherein each plant lighting sheet has a length and a width, wherein the plurality of lighting sheets is arranged along a length of a room;

a plurality of plant-holding pockets arranged along the length of the room generally parallel to the plurality of ducted plant-lighting plenum sheets; and a plant-lighting plenum sheets motion and withdrawal system arranged to move the plurality of ducted plant-lighting plenum sheets to a plurality of different locations relative to the plurality of plant-holding pockets for different time periods.

20. The apparatus of claim 19, further comprising:

a plurality of shelves, wherein the plurality of plant-holding pockets includes a plurality of pots configured to hold soil or soil substitute for growing plants, and wherein the pots of the plurality of pots are supported by the plurality of shelves.

21. The apparatus of claim 19, further comprising:

a support sheet supported vertically, wherein the plurality of plant-holding pockets are attached to or formed from the support sheet and each of the plurality of plant-holding pockets is configured to hold one or more crop plants during a growth period of the crop plants.

22. A gas-delivery lighting apparatus comprising:

a housing having a support structure;

a first circuit substrate having a first plurality of perforations, the first circuit substrate connected to the support structure on a first side of the support structure, wherein the first circuit substrate has a first plurality of conductors on a first face of the first circuit substrate;

a first plurality of LEDs affixed to the first plurality of conductors, wherein the first plurality of conductors form a parallel-series circuit with the first plurality of LEDs;

a second circuit substrate having a second plurality of perforations, the second circuit substrate connected to the support structure on a second side of the support structure, opposite the first side, wherein the second circuit substrate has a second plurality of conductors on a first face of the second circuit substrate;

a second plurality of LEDs affixed to the second plurality of conductors, wherein the second plurality of conductors form a parallel-series circuit with the second plurality of LEDs; and means for delivering a gas to the housing such that the gas is emitted out through the first plurality of perforations and out through the second plurality of perforations.

* * * * *